US009789087B2

(12) United States Patent
Bray et al.

(10) Patent No.: US 9,789,087 B2
(45) Date of Patent: Oct. 17, 2017

(54) PAR4 INHIBITOR THERAPY FOR PATIENTS WITH PAR4 POLYMORPHISM

(71) Applicant: THOMAS JEFFERSON UNIVERSITY, Philadelphia, PA (US)

(72) Inventors: Paul Bray, Philadelphia, PA (US); Michael Holinstat, Ann Arbor, MI (US); Leonard Edelstein, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 15/226,425

(22) Filed: Aug. 2, 2016

(65) Prior Publication Data

US 2017/0035734 A1    Feb. 9, 2017

Related U.S. Application Data

(60) Provisional application No. 62/200,180, filed on Aug. 3, 2015.

(51) Int. Cl.
A61K 31/416    (2006.01)
A61K 45/06     (2006.01)
A61K 31/616    (2006.01)
A61K 38/08     (2006.01)
C12Q 1/68      (2006.01)

(52) U.S. Cl.
CPC .......... *A61K 31/416* (2013.01); *A61K 31/616* (2013.01); *A61K 38/08* (2013.01); *A61K 45/06* (2013.01); *C12Q 1/6827* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,946,773 A | 8/1990 | Maniatis et al. | |
| 5,130,238 A | 7/1992 | Malek et al. | |
| 5,169,766 A | 12/1992 | Schuster et al. | |
| 5,846,710 A | 12/1998 | Bajaj | |
| 5,849,483 A | 12/1998 | Shuber | |
| 5,851,770 A | 12/1998 | Babon et al. | |
| 5,858,659 A | 1/1999 | Sapolsky et al. | |
| 5,866,337 A | 2/1999 | Schon | |
| 5,925,525 A | 7/1999 | Fodor et al. | |
| 5,928,870 A | 7/1999 | Lapidus et al. | |
| 5,952,172 A | 9/1999 | Meade et al. | |
| 5,968,740 A | 10/1999 | Fodor et al. | |
| 6,013,431 A | 1/2000 | Soderlund et al. | |
| 6,018,041 A | 1/2000 | Drmanac et al. | |
| 6,025,136 A | 2/2000 | Drmanac | |
| 6,210,891 B1 | 4/2001 | Nyren et al. | |
| 6,355,433 B1 | 3/2002 | Xu et al. | |
| 6,387,942 B2 | 5/2002 | Teng et al. | |
| 6,455,249 B1 | 9/2002 | Hsu et al. | |
| 6,458,535 B1 | 10/2002 | Hall et al. | |
| 6,472,157 B1 | 10/2002 | Di Rienzo et al. | |
| 6,864,229 B2 | 3/2005 | Kuliopulos et al. | |
| 7,514,465 B2 | 4/2009 | Kuo et al. | |
| 2002/0016293 A1 | 2/2002 | Ratain et al. | |
| 2003/0099960 A1 | 5/2003 | Ratain et al. | |
| 2004/0203034 A1 | 10/2004 | Ratain et al. | |
| 2013/0289238 A1 | 10/2013 | Kornacker et al. | |
| 2015/0094297 A1 | 4/2015 | Banville et al. | |
| 2015/0119390 A1* | 4/2015 | Martel | C07D 487/04 514/233.2 |
| 2015/0133446 A1 | 5/2015 | Lawrence et al. | |

FOREIGN PATENT DOCUMENTS

| | | |
|---|---|---|
| EP | 3329822 B1 | 6/1994 |
| WO | 8906700 A1 | 7/1989 |
| WO | 8910414 A1 | 11/1989 |
| WO | 9505142 A1 | 2/1995 |
| WO | 9810315 A1 | 3/1998 |
| WO | 0034283 A1 | 6/2000 |
| WO | 0180896 A2 | 11/2001 |
| WO | WO 2009007726 * | 1/2009 |
| WO | 2013163241 A1 | 10/2013 |
| WO | 2013163244 A1 | 10/2013 |

OTHER PUBLICATIONS

Edelstein, LC, et al, Common variants in the human platelet PAR4 thrombin receptor alter platelet function and differ by race, Blood. Nov. 27, 2014;124(23):3450-8. doi: 10.1182/blood-2014-04-572479. Epub Oct. 7, 2014 in view of Martel, A.*

Young, S.E., et al., "Synthesis of indole derived protease-activated receptor 4 antagonists and characterization in human platelets", PLOS One, vol. 8, No. 6, e65528, 2013.

Zhang, C., et al., "High-resolution crystal structure of human protease-activated receptor 1", Nature, vol. 492, No. 7429, pp. 387-392, 2012.

Zhang, D., et al., "Amplification of circularizable probes for the detection of target nucleic acids and proteins", Clinica Chimica Acta, vol. 363, Nos. 1-2, pp. 61-70, 2006.

Zhong, X., et al., "Single-nucleotide polymorphism genotyping on optical thin-film biosensor chips", Proc Natl Acad Sci, vol. 100, No. 20, pp. 11559-11564, 2003.

(Continued)

Primary Examiner — Thomas S Heard

(74) Attorney, Agent, or Firm — Cozen O'Connor

(57) ABSTRACT

Disclosed herein are methods for determining whether a PAR4 inhibitor should be administered to a human subject, the methods comprising administering a PAR4 inhibitor to a subject determined to have a "G" allele for a single-nucleotide polymorphism (SNP) at rs773902, and not administering a PAR4 inhibitor to a subject determined to have an "A" allele for the SNP at rs773902. A genotyping assay can be used to determine the SNP.

7 Claims, 7 Drawing Sheets

(56) References Cited

OTHER PUBLICATIONS

Zhu, J., et al., "Structure-Guided Design of a High-Affinity Platelet Integrin aMbp3 Receptor Antagonist That Disrupts Mg2+ Binding to the MIDAS", Sci Transl Med, vol. 4, No. 125, 125ra132, 2012.
Zhu, L., et al., "Regulated surface expression and shedding support a dual role for semaphorin 4D in platelet responses to vascular injury", Proc Natl Acad Sci U S A, vol. 104, No. 5, pp. 1621-1626, 2007.
Liew, M., et al., "Genotyping of Single-Nucleotide Polymorphisms by High-Resolution Melting of Small Amplicons", Clinical Chemistry, vol. 50, No. 7, pp. 1156-1164, 2004.
Livak, K.J., et al, "Allelic discrimination using fluorogenic probes and the 5' nuclease assay", Genet Anal., vol. 14, Nos. 5-6, pp. 143-149, 1999.
Lova, P., et al., "Contribution of protease-activated receptors 1 and 4 and glycoprotein lb-IX-V in the G(i)-independent activation of platelet Rap1B by thrombin", The Journal of Biological Chemistry, vol. 279, No. 24, pp. 25299-25306, 2004.
MacFarlane, S.R., et al., "Proteinase-activated receptors", Pharmacol Rev., vol. 53, No. 2, pp. 245-282, 2001.
McQuitty, C.K., et al., "Polymorphism in the human β2 adrenergic receptor gene detected by Restriction Endonuclease digestion with Fnu4HI, Human Genetics", vol. 93, No. 2, p. 225, 1994.
Muehlschlegel, J.D., et al., "Polymorphism in the protease-activated receptor-4 gene region associates with platelet activation and perioperative myocardial injury", Am J Hematol, vol. 87, No. 2, pp. 161-166, 2012.
Mumaw, M.M., et al., "Development and characterization of monoclonal antibodies against Protease Activated Receptor 4 (PAR4)", Thrombosis Research, vol. 135, pp. 1165-1171, 2015.
Myers, R.M., et al., "Detection of single base substitutions in total genomic DNA", Nature, vol. 313, pp. 495-498, 1985.
Myers, R.M., et al., "Detection of single base substitutions by ribonuclease cleavage at mismatches in RNA:DNA duplexes", Science, vol. 230, No. 4731, pp. 1242-1246, 1985.
Nagalla, S., et al., "Platelet microRNA-mRNA coexpression profiles correlate with platelet reactivity", Blood, vol. 117, No. 19, pp. 5189-5197, 2011.
Newton, C.R., et al., "Genetic analysis in cystic fibrosis using the amplification refractory mutation system (ARMS): the J3.11 MspI polymorphism", J Med Genet, vol. 28, pp. 248-251, 1991.
Nyren, P. et al., "Solid phase DNA minisequencing by an enzymatic luminometric inorganic pyrophosphate detection assay", Anal. Biochem.. vol. 208, pp. 171-175, 1993.
O'Donnell, C.J., et al., "Genetic and environmental contributions to platelet aggregation: the Framingham heart study", Circulation, vol. 103, No. 25, pp. 3051-3056, 2001.
Orita, M., et al., "Detection of polymorphisms of human DNA by gel electrophoresis as single-strand conformation polymorphisms", Proc. Natl. Acad. Sci. USA, vol. 86, pp. 2766-2770, 1989.
Pastinen, T., et al., "Multiplex, fluorescent, solid-phase minisequencing for efficient screening of DNA sequence variation", Clinical Chemistry, vol. 42, No. 9, pp. 1391-1397, 1996.
Peng, C.Y., et al., "The indazole derivative YD-3 inhibits thrombin-induced vascular smooth muscle cell proliferation and attenuates intimal thickening after balloon injury", Thromb Haemost, vol. 92, pp. 1232-1239, 2004.
Prezant, T.R., et al., "Trapped-oligonucleotide nucleotide incorporation (TONI) assay, a simple method for screening point mutations", Human Mutation, vol. 1, No. 2, pp. 159-164, 1992.
R Core Team, R: A Language and Environment for Statistical Computing, R Foundation for Statistical Computing, Vienna, Austria, 2013.
Rasmussen, S.G., et al., "Crystal structure of the β2 adrenergic receptor-Gs protein complex", Nature, vol. 477, No. 7366, pp. 549-555, 2011.
Rosenbaum, V., et al., "Temperature-gradient gel electrophoresis: Thermodynamic analysis of nucleic acids and proteins in purified form in cellular extracts", Biophysical Chemistry, vol. 26, pp. 235-246, 1987.
Rust, S., et al., "Mutagenlcally separated PCR (MS-PCR): a highly specific one step procedure for easy mutation detection", Nucleic Acids Research, vol. 21, No. 16, pp. 3623-3629, 1993.
Saleeba, J.A., et al., "Chemical cleavage of mismatch to detect mutations", Methods in Enzymology, vol. 217, pp. 286-295, 1993.
Sauer, S., "Typing of single nucleotide polymorphisms by MALDI mass spectrometry: Principles and diagnostic applications", Clinica Chimica Acta, vol. 363, Nos. 1-2, pp. 95-105, 2006.
Sauer, S., et al., "A novel procedure for efficient genotyping of single nucleotide polymorphisms", Nucleic Acids Research, vol. 28, No. 5, e13, 2000.
Sauer, S., et al., "Full flexibility genotyping of single nucleotide polymorphisms by the GOOD assay", Nucleic Acids Research, vol. 28, No. 23, e100, 2000.
Shalon, D., et al., "A DNA microarray system for analyzing complex DNA samples using two-color fluorescent probe hybridization", Genome Research, vol. 6, No. 7, pp. 639-645, 1996.
Shapiro, M.J., et al., "Role of the thrombin receptor's cytoplasmic tail in intracellular trafficking. Distinct determinants for agonist-triggered versus tonic internalization and intracellular localization", The Journal of Biological Chemistry, vol. 271, No. 51, pp. 32874-32880, 1996.
Shapiro, M.J., et al., "Protease-activated receptors 1 and 4 are shut off with distinct kinetics after activation by thrombin", The Journal of Biological Chemistry, vol. 275, No. 33, pp. 25216-25221, 2000.
Simon, L.M., et al. "Human platelet microRNA-mRNA networks associated with age and gender revealed by integrated plateletomics", Blood, vol. 123, No. 16, pp. e37-e45, 2014.
Sokolov, B. P., "Primer Extension Technique for the Detection of Single Nucleotide in Genomic DNA", Nucleic Acids Research, vol. 18, No. 12, p. 3671, 1990.
Solinas, A., et al., "Duplex Scorpion primers in SNP analysis and FRET applications", Nucleic Acids Research, vol. 29, No. 20, e96, 2001.
Suomalainen, A., et al., "Quantitative analysis of human DNA sequences by PCR and solid-phase minisequencing", Molecular Biotechnology, vol. 15, No. 2, pp. 123-131, 2000.
Syvanen, A.C., et al., "A primer-guided nucleotide incorporation assay in the genotyping of apolipoprotein E", Genomics, vol. 8, No. 4, pp. 684-692, 1990.
Tello-Montoliu, A., et al., "Antiplatelet therapy: thrombin receptor antagonists", British Journal of Clinical Pharmacology, vol. 72, No. 4, pp. 658-671, 2011.
Thelwell, N., et al., "Mode of action and application of Scorpion primers to mutation detection", Nucleic Acids Research, vol. 28, No. 19, pp. 3752-3761, 2000.
Thomas, K.L., et al., "Racial differences in long-term survival among patients with coronary artery disease", Am. Heart J., vol. 160, No. 4, pp. 744-751, 2010.
Tobe, V.O., et al., "Single-well genotyping of diallelic sequence variations by a two-color ELISA-based oligonucleotide ligation assay", Nucleic Acids Research, vol. 24, No. 19, pp. 3728-3732, 1996.
Tyagi, S., et al., "Multicolor molecular beacons for allele discrimination", Nature Biotechnology, Nature Publishing, US, vol. 16, pp. 49-53, 1998.
Ugozzoli, L., et al., "Detection of specific alleles by using allele-specific primer extension followed by capture on solid support", Genetic Analysis: Biomolecular Engineering, vol. 9, No. 4, pp. 107-112, 1992.
Ulvik, A., et al., "Single Nucleotide Polymorphism (SNP) Genotyping in Unprocessed Whole Blood and Serum by Real-Time PCR: Application to SNPs Affecting Homocysteine and Folate Metabolism", Clinical Chemistry, vol. 47, No. 11, pp. 2050-2053, 2001.
Vassallo, R.R., Jr., et al., "Structure-Function Relationships in the Activation of Platelet Thrombin Receptors by Receptor-Derived Peptides", J. Biol. Chem., vol. 267, pp. 6081-6085, 1992.
Von Ahsen, N., et al., Two for Typing: Homogeneous Combined Single-Nucleotide Polymorphism Scanning and Genotyping: Clinical Chemistry, vol. 51, No. 10, pp. 1761-1762, 2005.
Walker, G.T., et al., "Isothermal in vitro amplification of DNA by a restriction enzyme/DNA polymerase system", Proc. Natl. Acad. Sci. USA, vol. 89, pp. 392-396, 1992.

(56) References Cited

OTHER PUBLICATIONS

Weber, J.L., et al., "Human diallelic insertion/deletion polymorphisms", Am J Hum Genet., vol. 71, No. 4, pp. 354-862, 2002.
Wu, C.C., et al., "YD-3, a novel inhibitor of protease-induced platelet activation", British Journal of Pharmacology, vol. 130, No. 6, pp. 1289-1296, 2000.
Wu, C.C., et al., "Selective Inhibition of Protease-activated Receptor 4-dependent Platelet Activation by YD-3", Thrombosis and Haemostasis, vol. 87, No. 6, pp. 1026-1033, 2002.
Wu, C.C., et al., "The role of PAR4 in thrombin-induced thromboxane production in human platelets", Thrombosis and Haemostasis, vol. 90, No. 2, pp. 299-302, 2003.
Wu, C.C., et al., "Comparison of the effects of PAR1 antagonists, PAR4 antagonists, and their combinations on thrombin-induced human platelet activation", European Journal of Pharmacology, vol. 546, Nos. 1-3, pp. 142-147, 2006.
Xu, W.F., et al., "Cloning and characterization of human protease-activated receptor 4", Proc Natl Acad Sci U S A, vol. 95, No. 12, pp. 6642-6646, 1998.
Yeung, A.T., et al., "Enzymatic mutation detection technologies", BioTechniques, vol. 38, pp. 749-758, 2005.
Baron, H., et al., "Oligonucleotide Ligation Assay for Detection of Apolipoprotein E Polymorphisms", Clinical Chemistry, vol. 43, No. 10, pp. 1984-1986, 1997.
Bernard, K., et al., "Multiplex Messenger Assay: Simultaneous, Quantitative Measurement of Expression of Many Genes in the Context of T Cell Activation", Nucleic Acids Research, vol. 24, No. 8, pp. 1435-1442, 1996.
Berry, J.D., et al., "Lifetime risks of cardiovascular disease", The New England Journal of Medicine, vol. 366, No. 4, pp. 321-329, 2012.
Brass, L.F., et al., "Structure and Function of the Human Platelet Thrombin Receptor", J. Biol. Chem., vol. 267, No. 20, pp. 13795-13798, 1992.
Bray, P.F., et al., "Heritability of platelet function in families with premature coronary artery disease", J Thromb Haemost, vol. 5, No. 8, pp. 1617-1623, 2007.
Bray, P.F., et al., "Heritability of platelet reactivity in White and African American subjects at moderately high risk of aoronary artery disease", Circulation, vol. 112, 443a, 2005.
Castley, A., et al., "Clinical Applications of Whole-Blood PCR with Real-Time Instrumentation", Clinical Chemistry, vol. 51, No. 11, pp. 2025-2030, 2005.
Chackalamannil, S., et al., "Discovery of a novel, orally active himbacine-based thrombin receptor antagonist (SCH 530348) with potent antiplatelet activity", J Med Chem., vol. 51, No. 11, pp. 3061-3064, 2008.
Chen, X., et al., "A Homogeneous, Ligase-Mediated DNA Diagnostic Test", Genome Res., vol. 8, pp. 549-556, 1998.
Chen, X., et al., "Fluorescence polarization in homogeneous nucleic acid analysis", Genome Res., vol. 9, pp. 192-498, 1999.
Chintala, M., et al., "SCH 602539, a Protease-Activated Receptor-1 Antagonist, Inhibits Thrombosis Alone and in Combination With Cangrelor in a Folts Model of Arterial Thrombosis in Cynomolgus Monkeys", Arterioscler Thromb Vasc Biol, vol. 30, pp. 2143-2149, 2010.
Clark, A.G., "Inference of haplotypes from PCR-amplified samples of diploid populations", Mol. Biol. Evol., vol. 7, No. 2, pp. 111-122, 1990.
Cole, S.P.C., et al., "The EBV-Hybridoma Technique and its Application to Human Lung Cancer", in Monoclonal Antibodies and Cancer Therapy, Alan R. Liss Inc.), pp. 77-96, 1985.
Cotton, R.G.H., et al., "Reactivity of cytosine and thymine in single-base-pair mismatches with hydroxylane and osmium tetroxide and its application to the study of mutations", Proc. Natl. Acad. Sci. USA, vol. 85, pp. 4397-4401, 1988.
Cotton, R.G.H., "Current methods of mutation detection", Mutation Research, vol. 285, No. 1, pp. 125-144, 1993.

Coughlin, S.R., "Protease-activated receptors in hemostasis, thrombosis and vascular biology", J Thromb Haemost., vol. 3, No. 8, pp. 1800-1814, 2005.
Covic, L., et al., "Pepducin-based intervention of thrombin-receptor signaling and systemic platelet activation", Nature Medicine, vol. 8, No. 10, pp. 1161-1165, 2002.
Davis, M.W., et al., "Single-Nucleotide Polymorphism Mapping", Methods in Molecular Biology, vol. 351, pp. 75-92, 2006.
De Candia, E., et al., "Binding of thrombin to glycoprotein lb accelerates the hydrolysis of PAR1 on intact platelets", J Biol Chem., vol. 276, No. 7, pp. 4692-4698, 2001.
Derian, C.K., et al., "Blockade of the thrombin receptor protease-activated receptor-1 with a small-molecule antagonist prevents thrombus formation and vascular occlusion in nonhuman primates", Journal of Pharmacology and Experimental Therapeutics, vol. 304, No. 2, pp. 855-861, 2001.
Doris, P.A., et al., "Quantitative analysis of gene expression by ion-pair high-performance liquid chromatograph", J. Chromatogr. A., vol. 806, No. 1, pp. 47-60, 1998.
Dunbar, S.A., et al., "Rapid Screening for 31 Mutations and Polymorphisms in the Cystic Fibrosis Transmembrane Conductance Regulator Gene by Luminex® xMAP™ Suspension Array", Methods in Molecular Medicine, vol. 114, pp. 147-171, 2005.
Dunbar, S.A., "Applications of Luminex® xMAP™ technology for rapid, high-throughput multiplexed nucleic acid letection", Clinica Chimica Acta, vol. 363, Nos. 1-2, pp. 71-82, 2006.
Eagle, K.A., et al., "Identifying patients at high risk of a cardiovascular event in the near future: current status and future directions: report of a national heart, lung, and blood institute working group", Circulation, vol. 121, No. 12, pp. 1447-1454, 2010.
Edelstein, L.C., et al. "Racial differences in human platelet PAR4 reactivity reflect expression of PCTP and miR-376c", Nat Med., vol. 19, No. 12, pp. 1609-1616, 2013.
Gusella, J.F., "DNA Polymorphism and Human Disease", Annual Review of Biochemistry, vol. 55, pp. 831-854, 1986.
Hayashi, K., "PCR-SSCP: a method for detection of mutations", Genet Anal Tech Appl, vol. 9, No. 3, pp. 73-79, 1992.
Henriksen, R.A., et al., "PAR4 agonist AYPGKF stimulates thromboxane production by human platelets", Arterioscler Thromb Vasc Biol., vol. 22, No. 5, pp. 861-866, 2002.
Holinstat, M., et al., "PAR4, but not PAR1, signals human platelet aggregation via Ca2+ mobilization and synergistic P2Y12 receptor activation", J Biol Chem., vol. 281, No. 36, pp. 26665-266774, 2006.
Holland, P.M., et al., "Detection of specific polymerase chain reaction product by utilizing the 5'—3' exonuclease activity of Thermus aquaticus DNA polymerase", Proc Natl Acad Sci USA, vol. 88, pp. 7276-7280, 1991.
Hollenberg, M.D., et al., "Proteinase-activated receptor 4 (PAR4): activation and inhibition of rat platelet aggregation by PAR4-derived peptides", Can J Physiol Pharmacol, vol. 79, No. 5, pp. 439-442, 2001.
Husted, S., et al., "Pharmacodynamics, pharmacokinetics, and safety of the oral reversible P2Y12 antagonist AZD6140 with aspirin in patients with atherosclerosis: a double-blind comparison to clopidogrel with aspirin", European Heart Journal, vol. 27, No. 9, pp. 1038-1047, 2006.
Isberg, V, et al., "GPCRDB: an information system for G protein-coupled receptors", Nucleic Acids Research, vol. 42 (Database issue), pp. D422-D425, 2014.
Johnson, A.D., et al., "Genome-wide meta-analyses identifies seven loci associated with platelet aggregation in response to agonists", Nat. Genet., vol. 42, No. 7, pp. 608-613, 2010.
Kaufmann, R., et al., "Investigation of PAR-1-type Thrombin Receptors in Rat Glioma C6 Cells with a Novel Monoclonal Anti-PAR-1 Antibody (Mab COR7-6H9)", Journal of Neurocytolology, vol. 27, No. 9, pp. 661-666, 1998.
Keen, J., et al., "Rapid detection of singlebase mismatches as heteroduplexes on HydroLink gels", Trends Genet, vol. 7, p. 5, 1991.
Keen-Kim, D., et al., "Microelectronic array system for molecular diagnostic genotyping: Nanogen NanoChip® 400 and Molecular

(56) References Cited

OTHER PUBLICATIONS

Biology Workstation", Expert Review of Molecular Diagnostics, vol. 6, No. 3, pp. 287-294, 2006.

Kelley, S.O., et al., "Single-base mismatch detection based on charge transduction through DNA", Nucleic Acids Research, vol. 27, No. 24, pp. 4830-4837, 1999.

Kim, S., et al., Akt activation in platelets depends on Gi signaling pathways, J Biol Chem., vol. 279, No. 6, pp. 4186-4195, 2004.

Kohler, G., et al., "Continuous cultures of fused cells secreting antibody of predefined specificity", Nature, vol. 256, No. 5517, pp. 495-497, 1975.

Kokoris, M., et al., "High-throughput SNP Genotyping with the Masscode System", vol. 5, No. 4, pp. 329-340, 2000.

Kornher, J. S., et al., "Mutation detection using nucleotide analogs that alter electrophoretic mobility", Nucleic Acids Research, vol. 17, No. 19, pp. 7779-7784, 1989.

Kozbor, D., et al., "The production of monoclonal antibodies from human lymphocytes", Immunology Today, vol. 4, No. 3, pp. 72-79, 1983.

Kuppuswamy, M.N., et al., "Single nucleotide primer extension to detect genetic diseases: experimental application to hemophilia B (factor IX) and cystic fibrosis genes", Proc. Natl. Acad. Sci. USA, vol. 88, pp. 1143-1147, 1991.

Kwoh, D., et al., "Transcription-based amplification system and detection of amplified human immunodeficiency virus type 1 with a bead-based sandwich hybridization format", Proc. Natl. Acad Sci. USA, vol. 86, pp. 1173-1177, 1989.

Latif, S., et al., "Fluorescence Polarization in Homogeneous Nucleic Acid Analysis: II. 5-Nuclease Assay", Genome Res, vol. 11, pp. 436-440, 2001.

Lentes, K.U., et al., "A biallelic DNA polymorphism of the human beta-2-adrenergic receptor detected by Ban I-Adrbr-2", Nucleic Acids Research, vol. 16, No. 5, p. 2359, 1988.

Li, J., et al., "Single nucleotide polymorphism determination using primer extension and time-of-flight mass spectrometry", Electrophoresis, vol. 20, pp. 1258-1265, 1999.

Li, J.Z., et al., "Worldwide human relationships inferred from genome-wide patterns of variation", Science, vol. 319, No. 5866, pp. 1100-1104, 2008.

Li, Z, et al., "Signaling during platelet adhesion and activation", Arterioscler Thromb Vasc Biol., vol. 30, No. 12, pp. 2341-2349, 2010.

\* cited by examiner

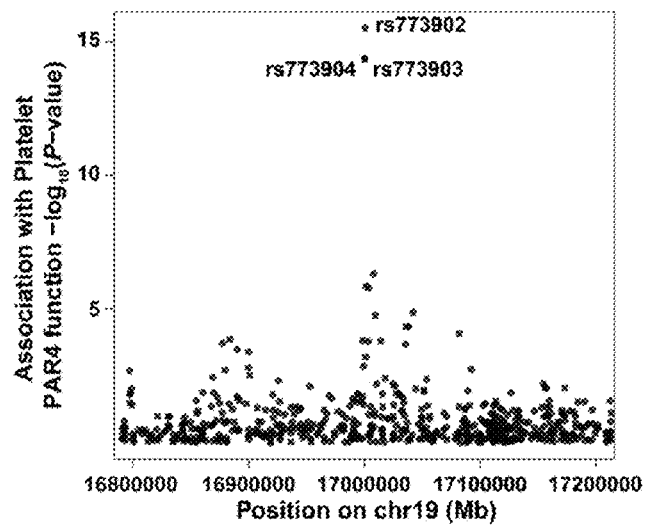
*FIG. 2A*
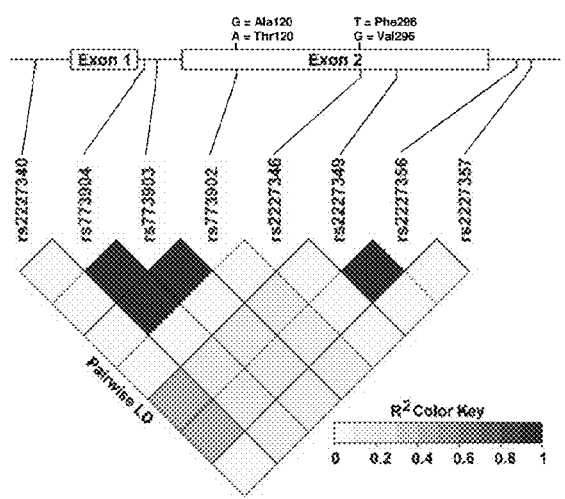
|  | Black | White |
|---|---|---|
| AA | 40% | 1% |
| AG | 46% | 35% |
| GG | 14% | 64% |
|  |  |  |
| A (Thr) freq | 63% | 19% |
| G (Ala) freq | 37% | 81% |
*FIG. 2C*
*FIG. 2B*

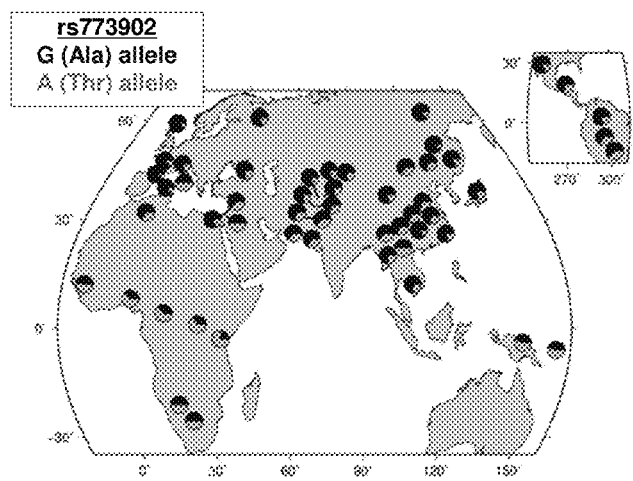
FIG. 2D
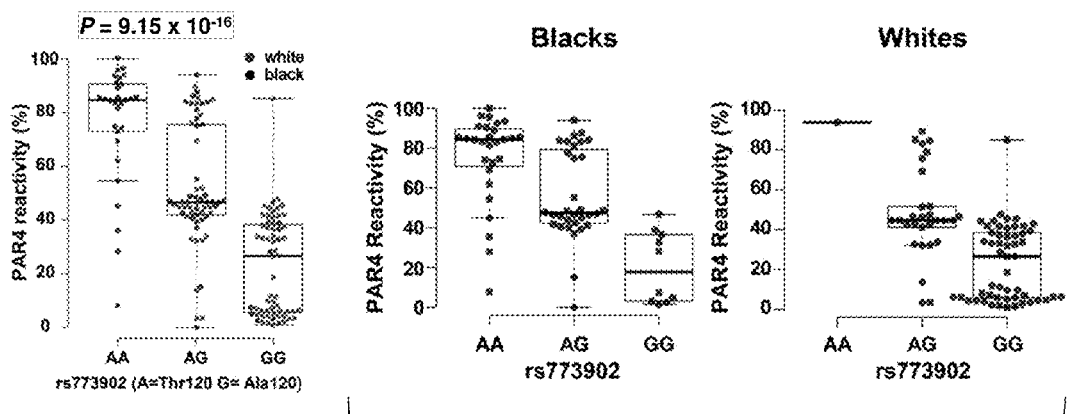
FIG. 3A
FIG. 3B

SEQUENCE LISTING

```
<160> NUMBER OF SEQ ID NOS: 1

<210> SEQ ID NO 1
<211> LENGTH: 385
<212> TYPE: PRT
<213> ORGANISM: Homo sapiens

<400> SEQUENCE: 1

Met Trp Gly Arg Leu Leu Leu Trp Pro Leu Val Leu Gly Phe Ser Leu
1               5                   10                  15

Ser Gly Gly Thr Gln Thr Pro Ser Val Tyr Asp Glu Ser Gly Ser Thr
            20                  25                  30

Gly Gly Gly Asp Asp Ser Thr Pro Ser Ile Leu Pro Ala Pro Arg Gly
        35                  40                  45

Tyr Pro Gly Gln Val Cys Ala Asn Asp Ser Asp Thr Leu Glu Leu Pro
    50                  55                  60

Asp Ser Ser Arg Ala Leu Leu Leu Gly Trp Val Pro Thr Arg Leu Val
65                  70                  75                  80

Pro Ala Leu Tyr Gly Leu Val Leu Val Val Gly Leu Pro Ala Asn Gly
                85                  90                  95
```

-continued

```
Leu Ala Leu Trp Val Leu Ala Thr Gln Ala Pro Arg Leu Pro Ser Thr
            100                 105                 110
Met Leu Leu Met Asn Leu Ala Thr Ala Asp Leu Leu Leu Ala Leu Ala
            115                 120                 125
Leu Pro Pro Arg Ile Ala Tyr His Leu Arg Gly Gln Arg Trp Pro Phe
            130                 135                 140
Gly Glu Ala Ala Cys Arg Leu Ala Thr Ala Ala Leu Tyr Gly His Met
145                 150                 155                 160
Tyr Gly Ser Val Leu Leu Leu Ala Ala Val Ser Leu Asp Arg Tyr Leu
                165                 170                 175
Ala Leu Val His Pro Leu Arg Ala Arg Ala Leu Arg Gly Arg Arg Leu
                180                 185                 190
Ala Leu Gly Leu Cys Met Ala Ala Trp Leu Met Ala Ala Ala Leu Ala
                195                 200                 205
Leu Pro Leu Thr Leu Gln Arg Gln Thr Phe Arg Leu Ala Arg Ser Asp
            210                 215                 220
Arg Val Leu Cys His Asp Ala Leu Pro Leu Asp Ala Gln Ala Ser His
225                 230                 235                 240
Trp Gln Pro Ala Phe Thr Cys Leu Ala Leu Leu Gly Cys Phe Leu Pro
                245                 250                 255
Leu Leu Ala Met Leu Leu Cys Tyr Gly Ala Thr Leu His Thr Leu Ala
                260                 265                 270
Ala Ser Gly Arg Arg Tyr Gly His Ala Leu Arg Leu Thr Ala Val Val
                275                 280                 285
Leu Ala Ser Ala Val Ala Phe Phe Val Pro Ser Asn Leu Leu Leu Leu
            290                 295                 300
Leu His Tyr Ser Asp Pro Ser Pro Ser Ala Trp Gly Asn Leu Tyr Gly
305                 310                 315                 320
Ala Tyr Val Pro Ser Leu Ala Leu Ser Thr Leu Asn Ser Cys Val Asp
                325                 330                 335
Pro Phe Ile Tyr Tyr Tyr Val Ser Ala Glu Phe Arg Asp Lys Val Arg
                340                 345                 350
Ala Gly Leu Phe Gln Arg Ser Pro Gly Asp Thr Val Ala Ser Lys Ala
            355                 360                 365
Ser Ala Glu Gly Gly Ser Arg Gly Met Gly Thr His Ser Ser Leu Leu
370                 375                 380
Gln
385
```

US 9,789,087 B2

PAR4 INHIBITOR THERAPY FOR PATIENTS WITH PAR4 POLYMORPHISM

PRIORITY CLAIM

This application claims the benefit of U.S. Provisional Application Ser. No. 62/200,180, filed Aug. 3, 2015, the disclosure of which is hereby incorporated by reference in its entirety.

GOVERNMENT SUPPORT

This invention was made with government support under Grant No. 5R01HL102482-04 and Grant No. 1R01MD007880-01, awarded by the National Institutes of Health. The government has certain rights in the invention.

TECHNICAL FIELD

The present invention relates to anti-platelet therapies, prevention and/or treatment of thrombosis, and single-nucleotide polymorphisms.

BACKGROUND

Platelets Race/ethnicity is an important factor in determining the outcome of coronary heart disease (CHD). Compared to patients of white race/ethnicity, blacks have a 2-fold higher incidence of CHD, and black race/ethnicity is an independent predictor of worse survival after CHD events even when confounding demographic, socioeconomic, and clinical factors are considered (Berry et al., N. Eng. J. Med. 2012, 366, 321-329; Thomas et al., Am. Heart J. 2010, 160, 744-751). Acute coronary events like myocardial infarction (MI) occur when an occlusive platelet thrombus forms at the site of a ruptured atherosclerotic plaque.

P2Y12 and thromboxane receptor inhibition with aspirin and thienopyridines are mainstays of anti-platelet therapy for arterial vascular disease. More recently, the protease-activated receptor (PAR) 1 inhibitor, vorapaxar, was approved for the secondary treatment of patients with prior MI and peripheral vascular disease. Although PAR4 inhibitors have been developed, none have been studied in humans. Thrombin signals through platelet PAR1 and PAR4. These receptors couple to Gq proteins leading to activation of phospholipase Cγ, hydrolysis of phosphoinositides and increased cytoplasmic calcium, resulting in activation of integrin αIIbβ3 and platelet aggregation. There are cellular phenotypic differences between PAR1 and PAR4. PAR1 has a higher affinity for thrombin, and $Ca^{2+}$ transients rise sharply after PAR1 activation with PAR1-activating peptide (PAR1-AP) followed by a fast return to baseline levels. PAR4 stimulation with PAR4-activating peptide (PAR4-AP) induces a more gradual but sustained rise in $[Ca^{2+}]$, which accounts for the majority of intracellular calcium flux. PAR1 blockade with vorapaxar leaves PAR4 as the only means by which thrombin can activate platelets. PAR4 inhibition has a potential therapeutic advantage of inhibiting the maximal thrombin effect while minimizing bleeding because PAR1 signaling remains intact.

SUMMARY OF THE INVENTION

The invention is based, in part, on the discovery that a single-nucleotide polymorphism (SNP) at rs773902 can affect an individual's response to a protease-activated receptor 4 (PAR4) inhibitor. Specifically, for an individual with a "G" allele at rs773902, PAR4 inhibitors can be effective; for an individual with an "A" allele at rs773902, PAR4 inhibitors are less effective and should be avoided due to the risk of bleeding.

Accordingly, provided herein is a method of preventing or treating thrombosis in a human subject in need thereof, the method comprising administering a PAR4 inhibitor to a subject determined to have a "G" allele for a single-nucleotide polymorphism (SNP) at rs773902, and not administering a PAR4 inhibitor to a subject determined to have an "A" allele for the SNP at rs773902.

Further provided herein is a method of preventing or treating thrombosis in a human subject who is (a) being administered a PAR1 inhibitor and (b) has a "G" allele for a single-nucleotide polymorphism (SNP) at rs773902; the method comprising (a) stopping administration of the PAR1 inhibitor and (b) administering a therapeutically effective amount of a PAR4 inhibitor.

Also provided herein is a method of improving therapy for treating thrombosis in a human subject who is (a) being administered a PAR1 inhibitor and (b) has a "G" allele for a single-nucleotide polymorphism (SNP) at rs773902; the method comprising (a) stopping administration of the PAR1 inhibitor and (b) administering a therapeutically effective amount of a PAR4 inhibitor.

Further provided herein is a method of preventing or treating thrombosis in a human subject who is (a) being administered a P2Y12 inhibitor and (b) has a "G" allele for a single-nucleotide polymorphism (SNP) at rs773902; the method comprising (a) stopping administration of the P2Y12 inhibitor and (b) administering a therapeutically effective amount of a PAR4 inhibitor. In various embodiments, the P2Y12 inhibitor is clopidogrel, prasugrel, ticagrelor, or cangrelor, or a salt thereof.

A method of preventing or treating thrombosis in a human subject comprising: (a) subjecting a test sample obtained from the human subject to a genotyping assay adapted to determine the genotype of the SNP at rs773902; (b) determining whether the polymorphism at rs773902 has a "G" allele or an "A" allele, and (c) administering to a patient having a "G allele a PAR4 inhibitor and administering to said patient with the "A" allele a therapeutic that is not a PAR4 inhibitor.

Also provided herein is a method of improving therapy for treating thrombosis in a human subject who is (a) being administered a P2Y12 inhibitor and (b) has a "G" allele for a single-nucleotide polymorphism (SNP) at rs773902; the method comprising (a) stopping administration of the P2Y12 inhibitor and (b) administering a therapeutically effective amount of a PAR4 inhibitor. In various embodiments, the P2Y12 inhibitor is clopidogrel, prasugrel, ticagrelor, or cangrelor, or a salt thereof.

In some cases, the PAR4 inhibitor can be a compound as disclosed in WO 13/163244 (e.g., compound of any one of Examples 1-428). In various cases, the PAR4 inhibitor is a compound recited in Table 2 or Table 3 of WO 13/163244. In some cases, the PAR4 inhibitor is selected from the group consisting of Examples 205, 307, 316, 318, 319, 320, 325, 327, 346, 347, 350, 353, 355, 356, 358, 363, 370, 376, 383, 384, 386, 392, 394, 398, 399, 402, 404, 405, 407, 426 and 428, of WO 13/163244. In various cases, the PAR4 inhibitor is Example 203 or 205 of WO 13/163244. In some cases, the PAR4 inhibitor is a compound as disclosed in WO 13/163241 (e.g., Examples 1-114). In various cases, the PAR4 inhibitor is a compound recited in Table 1 or 2 of WO 13/163241. In some cases, the PAR4 inhibitor is a compound selected from the group consisting of Examples 13, 18, 23, 26, 28, 29, 30, 31, 40, 48, 53, 60, 64, 69, 71, 93, 97, 98, 100, and 110, of WO 13/163241. In various cases, the PAR4 inhibitor is selected from the group consisting of ethyl 4-(1-benzyl-1H-indazol-3-yl)benzoate (YD-3), trans-cinnamoyl-YPGKF-amide, P4pal-i1, and palmitoyl-SGRRY-GHALR-amide (P4pal-10).

In some embodiments, the method further comprises a step of subjecting a test sample obtained from the human subject to a genotyping assay adapted to determine the genotype of the SNP at rs773902. In some embodiments, the test sample is a blood sample, a urine sample, a buccal sample, a saliva sample, or a hair sample.

In some embodiments, the thrombosis is associated with coronary artery disease, stroke, vascular thrombosis, arterial thrombosis, atherothrombosis, deep vein thrombosis, peripheral vascular disease, peripheral arterial disease, or an inflammatory disease.

In various embodiments, the subject is further administered a P2Y12 inhibitor. In some embodiments, the P2Y12 inhibitor is clopidogrel, prasugrel, ticagrelor, or cangrelor, or a salt thereof. In various embodiments, the subject is further administered a therapeutically effective amount of aspirin.

BRIEF DESCRIPTION OF THE DRAWINGS

(FIG. 1A) PAR4 ARS values of PRAX1 subjects by self-identified race. $P=6.8 \times 10^{-9}$, 2-tailed T-test. (FIG. 1B) Microarray analysis of F2RL3 gene expression. Values are normalized and $\log_2$ transformed. P=0.043, 2-tailed T-test. (FIG. 1C) PAR4 protein levels normalized to GAPDH. P=0.0427, 1-tailed T-test. (FIG. 1D) Correlation analysis of platelet PAR4 reactivity with PAR4 protein expression level.

FIGS. 2A-2D show association of racially dimorphic PAR4 variants with platelet PAR4 function. (FIG. 2A) Manhattan plot showing association of SNPs in the F2RL3 gene with platelet PAR4-AP reactivity. Each circle represents a SNP. The circles for rs773903 and rs773904 overlap. Y-axis is −log 10 of the P-values for association, controlling for age, race, and sex; x-axis, chromosomal location. (FIG. 2B) Schematic of F2RL3 and linkage disequilibrium (LD) plot of SNPs in F2RL3. Non-synonymous SNPs coding changes are shown above schematic. Light grey rs numbers indicate SNPs identified in QTL analysis; Dark grey rs number indicates less common SNP observed only in black subjects. (FIG. 2C) Genotype and allele frequency of rs773902 in black and white PRAX1 subjects. (FIG. 2D) Worldwide allele frequency of rs773902 in HGDP dataset.

FIGS. 3A-3E show PAR4 variants and platelet function. Platelet PAR4 reactivity by rs773902 genotype for (FIG. 3A) all subjects and (FIG. 3B) for each race individually. $P=9.15 \times 10^{-16}$, association of PAR4 reactivity with rs773902 genotype by linear regression. (FIG. 3C) Platelet ARS of PRAX1 subjects for arachidonic acid (AA), ADP, collagen-related peptide (CRP), α-CD9 antibody (CD9), PAR1-AP (PAR1), and PAR4-AP (PAR4), segregated by rs773902 genotype. One-way ANOVA analysis showed no association of platelet function with rs773902 was observed for any agonist except PAR4-AP (PAR4-AP [panel A] is shown again for ease of comparison). (FIG. 3D) Platelet calcium flux from subjects genotyped for rs773902 (cohort 2). Platelets were treated with 50 μM PAR4-AP. n=10 GG; n=5 AA/AG. P=0.03 one-tailed T-test. (FIG. 3E) Platelet PAR4 reactivity by rs773902 and rs2227346 genotypes among self-identified black subjects in PRAX1. $P=1.75 \times 10^{-8}$, association of PAR4 reactivity with rs2227346 genotype partial F-test after controlling for rs773902 genotype. For all panels, box=interquartile range; horizontal line in box is median; whiskers is 1.5×interquartile range.

(FIG. 4A) Representative flow cytometry tracings for surface FLAG-PAR4 expression. 120A-296V indicates the expression construct for PAR4-Ala120-Val296; 120A-296F, for PAR4-Ala120-Phe296; 120T-296F, for PAR4-Thr120-Phe296; and 120T-296V, for PAR4-Thr120-Val296; Dark grey=α-FLAG; Light grey=IgG control. (FIG. 4B) $IP_3$ generation in 293 cells transfected with FLAG-PAR4 variants or control stimulated with 1 mM PAR4-AP. $IP_3$ levels were normalized to cell number and PAR4 surface expression. For each independent experiment all data points were calculated relative to the $IP_3$ quantified in the PAR4-Thr120-Phe296 expressing cells after 30 sec treatment (i.e., the maximum value measured in all experiments [% of Max $IP_3$ level]). n=3. P-value for 120T-296F vs. 120A-296F at 30 s=0.01, two-tailed T-test.

(FIG. 6A) Surface expression of FLAG-tagged PAR4 variants or empty vector into 293 HEK cells was determined by staining with FITC-α-FLAG antibody and flow cytometry. Surface expression of each variant was quantified using mean fluorescent intensity (MFI). IgG=Flow cytometry isotype control. No difference in surface expression between the variants was observed (One-way ANOVA, P=0.6543). (FIG. 6B) Individual plots of absolute quantification $IP_3$ generation in 293 cells transfected with PAR4 variants in response to PAR4-AP stimulation. Normalized and combined data is shown in FIG. 4B.

DETAILED DESCRIPTION

Figure 1A:
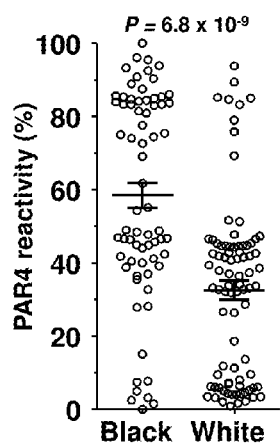
FIGS. 1A-1D show SNPs in F2RL3 associate with PAR4 reactivity.

Human platelets express two thrombin receptors, PAR1 and PAR4. Quantitative trait locus analysis identified three common SNPs in the PAR4 gene (F2RL3) associated with PAR4-induced platelet aggregation. Among these SNPs, rs773902 determines whether residue 120 in transmembrane domain 2 of the PAR4 polypeptide is an alanine (Ala) or threonine (Thr). rs773902 is located in the second exon. The "G" allele of rs773902 encodes alanine (Ala) and the "A" allele encodes threonine (Thr). Compared to the Ala120 variant, Thr120 is more common in black than white subjects (63% vs. 19%), and is associated with higher PAR4-induced human platelet aggregation and $Ca^{2+}$ flux, and generated greater inositol 1,4,5-triphosphate ($IP_3$) in transfected cells. A second, less frequent F2RL3 variant, Phe296Val, was only observed in blacks and abolished the enhanced PAR4-induced platelet aggregation and $IP_3$ generation associated with PAR4-Thr120. For reference, SEQ ID NO:1 corresponds to the amino acid sequence of the PAR4 polypeptide.

And thus the invention is based, in part, on the discovery that a single-nucleotide polymorphism (SNP) at rs773902 can affect an individual's response to a PAR4 inhibitor. Specifically, for an individual with a "G" allele at rs773902, PAR4 inhibitors can be effective; for an individual with an "A" allele at rs773902, PAR4 inhibitors are less effective and should be avoided due to the risk of bleeding. This SNP at rs773902 can be used to identify subjects with thrombosis or a risk of developing thrombosis that would benefit from or respond to a treatment regimen comprising a PAR4 inhibitor. Accordingly, the embodiments described herein are generally related to methods for preventing or treating thrombosis in a human subject in need thereof.

One aspect of the invention provides a method for preventing or treating thrombosis in a human subject in need thereof, the method comprising administering a PAR4 inhibitor to a subject determined to have a "G" allele for a single-nucleotide polymorphism (SNP) at rs773902, and not administering a PAR4 inhibitor to a subject determined to have an "A" allele for the SNP at rs773902.

In some embodiments, the method further comprises a step of subjecting a test sample obtained from the human subject to a genotyping assay adapted to determine the genotype of the SNP at rs773902. In some embodiments, the genotyping assay can comprise the step of amplifying the test sample with a set of primers flanking the SNP. Genotyping assays for the F2RL3 gene are commercially available at companies such as Life Technologies (e.g., TAQ-MAN® SNP genotyping assays).

Thrombosis is the formation of a blood clot inside a blood vessel. There are two forms of thrombosis: venous thrombosis and arterial thrombosis. Venous thrombosis can be classified into various subtypes including deep vein thrombosis, portal vein thrombosis, renal vein thrombosis, jugular vein thrombosis, Budd-Chiari syndrome, Paget-Schroetter disease, and cerebral venous sinus thrombosis. Arterial thrombosis can be classified into various subtypes including stroke, myocardial infarction, and infarction at other sites. In some embodiments, the thrombosis is associated with coronary artery disease, stroke, vascular thrombosis, peripheral vascular disease, inflammatory disease (e.g., arthritis).

In some embodiments, a human subject in need thereof can be a person diagnosed with having thrombosis. For example, the person can be having a stroke or heart attack. In some embodiments, a human subject in need thereof can be a person exhibiting one or more symptoms indicative of a thrombotic condition. In some embodiments, a human subject in need thereof can be a person having an increased risk of developing thrombosis.

PAR4 Inhibitors

Any PAR4 inhibitor can be used in this invention. Examples of PAR4 inhibitors include, but are not limited to, ethyl 4-(1-benzyl-1H-indazol-3-yl)benzoate (also known as YD-3), trans-cinnamoyl-YPGKF-amide, P4pal-i1, palmitoyl-SGRRYGHALR-amide (also known as P4pal-10), or a combination thereof. YD-3 as a PAR4 inhibitor was disclosed in Wu et al., British Journal of Pharmacology 2000, 130, 1289-1296. The chemical structure of YD-3 is shown below for reference:

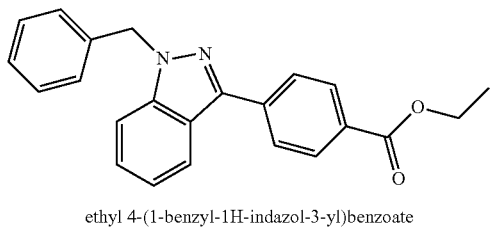

(YD-3)

ethyl 4-(1-benzyl-1H-indazol-3-yl)benzoate

PAR4 inhibitors are also disclosed, for example, in U.S. Pat. No. 6,387,942, U.S. Pat. No. 6,864,229, U.S. Pat. No. 7,514,465, US20130289238, US20150133446, US20150119390, US20150094297, WO 2013/163244, WO 2013/163241, the contents of each of which are incorporated by reference in their entirety.

Specific examples of PAR4 inhibitors contemplated include compounds of formula (I):

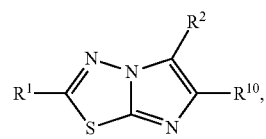

wherein R10 is

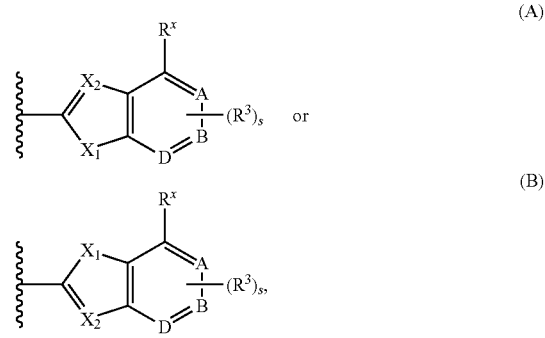

such as

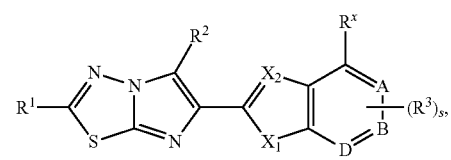

with substituents as defined in WO 13/163244, or specific compounds as listed in WO 13/163244 as any one of Examples 1-428, e.g., Example 203

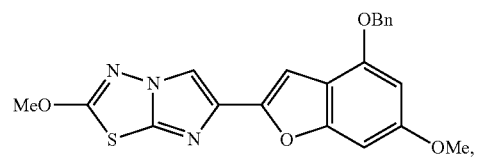 [SMILES: COc1cc(OCc2ccccc2)c2cc(-c3cn4nc(OC)sc4n3)oc2c1]

or Example 205

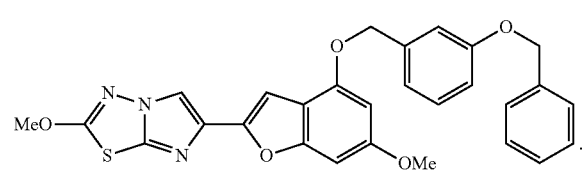 [SMILES: COc1cc(OCc2cccc(OCc3ccccc3)c2)c2cc(-c3cn4nc(OC)sc4n3)oc2c1]

Specific contemplated compounds include one or more compounds as recited in Table 2 or in Table 3 (in particular compounds 205, 307, 316, 318, 319, 320, 325, 327, 346, 347, 350, 353, 355, 356, 358, 363, 370, 376, 383, 384, 386, 392, 394, 398, 399, 402, 404, 405, 407, 426 and 428) of WO 13/163244.

Other specific compounds contemplated include those as disclosed in WO 13/163241, e.g., compounds having a structure:

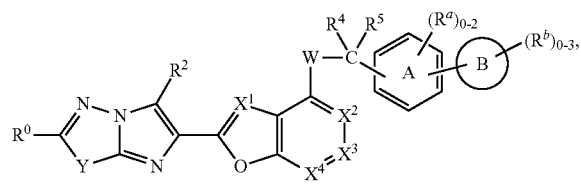

with substituents as desribed in WO 13/163241. In particular, compounds as disclosed in WO 13/163241 contemplated for the methods disclosed herein include structures of Formulae IA, IAA, IB, IC, ID, IE, IF, IG, IH, IJ, IK, IL, IM, IP, and IQ as dislcosed in WO 13/163241, and specific compounds of Examples 1-114, in particualr compounds as listed in Table 1 or Table 2, and more specifically compounds of Examples 13, 18, 23, 26, 28, 29, 30, 31, 40, 48, 53, 60, 64, 69, 71, 93, 97, 98, 100, and 110.

PAR1 Inhibitors

Any PAR1 inhibitor can be used in this invention. A PAR1 inhibitor can be a peptide, a peptide mimetic, a small molecule, an aptamer, a siRNA, a polynucleotide or an antibody. Examples of specific PAR1 inhibitors contemplated include vorapaxar (SCH-530348), atopaxar (E5555), and SCH-79797 (N3-cyclopropyl-7-{[4(I-methylethyl)phenyl]methyl)-7H-pyrrolo[3,2-f]quinaz-oline-I,3-diamine (CAS 245520-69-8)), SCH-602539 (Chintala, M. et al Arterioscler Thromb Vasc Biol (2010), 30, 2143-2149); and RWJ-56110.

Specific PAR1 antagonist antibodies have been disclosed in the art and are specifically contemplated for use in the methods disclosed herein. See for instance R. R. Vassallo, Jr. et al. "Structure-Function Relationships in the Activation of Platelet Thrombin Receptors by Receptor-Derived Peptides," J. Biol. Chem. 267:6081-6085 (1992) ("Vassallo, Jr. et al. (1992)"); L. F. Brass et al., "Structure and Function of the Human Platelet Thrombin Receptor," J. Biol. Chem. 267: 13795-13798 (1992) ("Brass et al. (1992)"); and R. Kaufmann et al., "Investigation of PAR-1-Type Thrombin Receptors in Rat Glioma C6 Cells with a Novel Monoclonal Anti-PAR-I Antibody (Mab COR7-6H9), J. Neurocytol. 27:661-666 (1998) ("Kaufmann et al. (1998)"), which are incorporated herein by reference. Specific examples of monoclonal antibodies include, but are not limited to: the monoclonal antibody designated ATAP2 in Brass et al. (1992); the monoclonal antibody designated ATAP120 in Brass et al. (1992); and a monoclonal antibody designated ATAP138 in Brass et al. (1992). Additionally, monoclonal antibodies contemplated include monoclonal antibodies that specifically bind either or both of the peptides used by Brass et al. (1992). Additionally, monoclonal antibodies contemplated include monoclonal antibodies that have complementary-determining regions that are identical to those of ATAP2, ATAP120, or ATAP138. Kaufmann et al. (1998) described monoclonal antibodies to rat PAR1 receptor that were prepared by using a peptide with a sequence described as being below the thrombin cleavage site for the receptor.

Specific PAR1 antagonist antibodies include analogous antibodies can prepared against the corresponding region of human PAR1 receptor. General methods for preparation of monoclonal or polyclonal antibodies are well known in the art. See, e.g., Harlow & Lane, Using Antibodies, A Laboratory Manual, Cold Spring Harbor Laboratory Press, Cold Spring Harbor, N.Y., 1998; Kohler & Milstein, Nature 256:495-497 (1975); Kozbor et al., Immunology Today 4:72 (1983); and Cole et al., pp. 77-96 in Monoclonal Antibodies and Cancer Therapy, 1985.

P2Y12 Inhibitors

The term "P2Y12 inhibitor", refers to the ability of a compound that can alter the function of P2Y12 receptors. A P2Y12 inhibitor may inhibit the activity of a P2Y12 receptor depending on the concentration of the compound exposed to the P2Y12 receptor, or may inhibit the activity of a P2Y12 receptor. Such inhibition may be contingent on the occurrence of a specific event, such as activation of a signal transduction pathway, and/or may be manifest only in particular cell types. In some embodiments, inhibition of P2Y12 activity may be assessed using the method described in Husted et al., Eur. Heart J. 2006, 27(9), 1038-1047; WO 2000034283; WO 199905142.

Examples of P2Y12 receptor inhibtors include, but are not limited to clopidogrel, prasugrel, cangrelor, and ticagrelor.

Dosing and Administration

The route and frequency of the administration, and dosage should depend on the particular PAR4 inhibitor and factors such as the age, gender, ethnicity of the subject.

The dosage can be determined by one of skill in the art and can also be adjusted by the individual physician in the event of any complication. Typically, the dosage of a PAR4 inhibitor can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

More information on dosages and administration methods can be found, for example, in "Remington: The Science and Practice of Pharmacy," 20th edition, Gennaro, Lippincott (2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards.

Other diseases or conditions that can benefit from determining the genotype at rs773902 include, but are not limited to, diseases mediated by endothelial cell PAR4 such as cancer metastases, preeclampsia, and eclampsia.

Test Sample and Collection and Preparation Thereof

Collections of test samples for at least one analysis performed in the methods described herein are well known to those skilled in the art. In some embodiments, a test sample subjected to analysis performed in the methods described herein are derived from a biological sample of a subject. The term "biological sample" as used herein denotes a sample taken or isolated from a biological organism, e.g., cell lysate, a homogenate of a tissue sample from a subject or a fluid sample from a subject. The term "biological sample" also includes untreated or pre-treated (or pre-processed) biological samples. In some embodiments, the biological sample can be a biological fluid, including, but not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In other embodiments, the biological sample can include cell lysate and fractions thereof. For example, cells (such as red blood cells, platelets, white blood cells and any cells circulating in the biological fluid described herein) can be harvested and lysed to obtain a cell lysate. In some embodiments, a test sample or a biological sample is a blood sample. In some embodiments, a test sample or a biological sample is a plasma sample. In some embodiments, a test sample or a biological sample is a saliva sample. In some embodiments, a test sample or a biological sample is a buccal sample. In some embodiments, a test sample or a biological sample is a urine sample. In some embodiments, a test sample or a biological sample is a hair sample.

A "biological sample" can contain cells from subject, but the term can also refer to non-cellular biological material, such as non-cellular fractions of blood, saliva, or urine, that can be used to determine SNPs. In some embodiments, the sample is from a resection, biopsy, or core needle biopsy. In addition, fine needle aspirate samples can be used. Samples can be either paraffin-embedded or frozen tissue.

The sample can be obtained by removing a sample of cells from a subject, but can also be accomplished by using previously isolated cells (e.g. isolated by another person). In addition, the biological sample can be freshly collected or a previously collected sample.

In some embodiments, the test sample or the biological sample can be a frozen biological sample, e.g., a frozen tissue or fluid sample such as urine, blood, serum or plasma. The frozen sample can be thawed before employing methods described herein. After thawing, a frozen sample can be centrifuged before being subjected to methods described herein.

In some embodiments, a test sample or a biological sample can be a nucleic acid product amplified after polymerase chain reaction (PCR). The nucleic acid product can include DNA, RNA and mRNA and can be isolated from a particular biological sample using any of a number of procedures, which are well-known in the art, the particular isolation procedure chosen being appropriate for the particular biological sample. Methods of isolating and analyzing nucleic acid variants as described above are well known to one skilled in the art and can be found, for example in the Molecular Cloning: A Laboratory Manual, 3rd Ed., Sambrook and Russel, Cold Spring Harbor Laboratory Press, 2001.

In some embodiments, the test sample or the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

The skilled artisan is well aware of methods and processes appropriate for pre-processing of test or biological samples, e.g., blood, required for determination of SNPs as described herein.

In some embodiments, the test sample or biological sample is a blood sample, e.g., whole blood, plasma, and serum. In some embodiments, the test sample or biological sample is a whole blood sample. In some embodiments, the test sample or biological sample is a serum sample. In some embodiments, the test sample or biological sample is a plasma sample. In some embodiments, the blood sample can be allowed to dry at room temperature from about 1 hour to overnight, or in the refrigerator (low humidity) for up to several months before subjected to analysis, e.g., SNP analysis. See, for example, Ulvik A. and Ueland P. M. (2001) Clinical Chemistry 47: 2050, for methods of SNP genotyping in unprocessed whole blood and serum by real-time PCR.

Methods for collecting different types of a test sample are known in the art and can be employed to prepare a test sample for the methods described herein.

SNPs, Polymorphisms and Alleles

The genomes of all organisms undergo spontaneous mutation in the course of their continuing evolution, generating variant forms of progenitor genetic sequences (Gusella, Ann. Rev. Biochem. 55, 831-854 (1986)). The coexistence of multiple forms of a genetic sequence gives rise to genetic polymorphisms, including SNPs.

Approximately 90% of all polymorphisms in the human genome are SNPs. SNPs are single base positions in DNA at which different alleles, or alternative nucleotides, exist in a population. The SNP position (interchangeably referred to herein as SNP, SNP site, SNP allele or SNP locus) is usually preceded by and followed by highly conserved sequences of the allele (e.g., sequences that vary in less than $\frac{1}{100}$ or $\frac{1}{1000}$ members of the populations). An individual can be homozygous or heterozygous for an allele at each SNP position. A SNP can, in some instances, be referred to as a "cSNP" to denote that the nucleotide sequence containing the SNP is an amino acid coding sequence.

A SNP can arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP can also be a single base insertion or deletion variant referred to as an "in/del" (Weber et al., "Human diallelic insertion/deletion polymorphisms", Am J Hum Genet October 2002; 71(4):854-62).

A synonymous codon change, or silent mutation/SNP (the terms "SNP" and "mutation" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

A major database of human SNPs is maintained at NCBI as db SNP, and it contains data for unique human SNPs consisting of $1.78 \times 10^8$ submitted SNP (identified by an "ss" number) and $5.2 \times 10^7$ reference SNP (identified by an "rs" number), as of Build History 135: human 9606 based on NCBI human genome build 37.3. The rs numbers are unique, do not change and allow analysis of the particularly identified SNP in any genetic sample. Throughout the specification, the SNPs described herein can also be identified by an "rs" number. For example, rs773902 corresponds to a SNP locus at position 16889821 of Chromosome 19 (http://www.ncbi.nlm.nih.gov/projects/SNP/snp_ref.cgi?rs=rs773902). With the "rs" numbers known for each SNP, one of skill in the art will be able to determine the position of a specific SNP within a respective chromosome.

While a SNP could conceivably have three or four alleles, nearly all SNPs have only two alleles. The SNP at rs773902 described herein have two alleles: "A" or "G". The presence of the "G" allele is more common in white people than in black people, while the presence of the "A" allele is more common in black people than in white people. A person with the "G" allele at rs773902 can benefit from a treatment regimen comprising a PAR4 inhibitor if the person is having thrombosis or at risk of developing thrombosis. A person with the "A" allele at rs773902 should avoid PAR4 inhibitors because the risk of bleeding outweighs the therapeutic benefit.

Those skilled in the art will readily recognize that nucleic acid molecules can be double-stranded molecules and that reference to a particular site on one strand refers, as well, to the corresponding site on a complementary strand. In defining a SNP position, SNP allele, or nucleotide sequence, reference to an adenine "A", a thymine "T" (uridine "U"), a cytosine "C", or a guanine "G" at a particular site on one strand of a nucleic acid molecule also defines the thymine "T" (uridine "U"), adenine "A", guanine "G", or cytosine "C" (respectively) at the corresponding site on a complementary strand of the nucleic acid molecule. Thus, reference can be made to either strand in order to refer to a particular SNP position, SNP allele, or nucleotide sequence. Probes and primers can be designed to hybridize to either strand and SNP genotyping methods disclosed herein can generally target either strand.

Accordingly, the claims are intended to cover analysis of the opposite strand as well. For the opposite-strand analysis, the SNP at rs773902 is the "T" allele or "C" allele.

Identification method of SNPs can be of either a positive-type (inclusion of an allele) or a negative-type (exclusion of an allele). Positive-type methods determine the identity of a nucleotide contained in a polymorphic site, whereas negative-type methods determine the identity of a nucleotide not present in a polymorphic site. Thus, a wild-type site can be identified either as wild-type or not mutant. For example, at a biallelic polymorphic site where the wild-type allele contains thymine and the mutant allele contains cytosine, a site can be positively determined to be either thymine or cytosine or negatively determined to be not thymine (and thus cytosine) or not cytosine (and thus thymine).

Methods for Detecting the SNPs Disclosed Herein

Substantially any method of detecting any allele of the SNPs described herein, such as restriction enzyme digestion, allele-specific probe hybridization, allele-specific primer extension, allele specific amplification, sequencing, 5' nuclease digestion, molecular beacon assay, oligonucleotide ligation assay, size analysis, and single-stranded conformational polymorphism, can be used.

In some embodiments, restriction enzymes can be utilized to identify variances or a polymorphic site using "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resulting restriction fragments are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment, restriction site analysis of particular nucleotide sequence to identify a nucleotide at a polymorphic site is determined by the presence or absence of a restriction enzyme site. A large number of restriction enzymes are known in the art and, taken together, they are capable of recognizing at least one allele of many polymorphisms. However, such single nucleotide polymorphisms (SNPs) rarely result in changes in a restriction endonuclease site. Thus, SNPs are rarely detectable by restriction fragment length analysis.

In some embodiments, ligation based assays can be utilized to identify variances or a polymorphic site. A number of approaches use DNA ligase, an enzyme that can join two adjacent oligonucleotides hybridized to a DNA template. In Oligonucleotide Ligation Assay (OLA) the sequence surrounding the mutation site is first amplified and one strand serves as a template for three ligation probes, two of these are ASO (allele-specific oligonucleotides) and a third common probe. Numerous approaches can be used for the detection of the ligated products, for example the ASOs with differentially labeled with fluorescent of hapten labels and ligated products detected by fluorogenic of colorimetric enzyme-linked immunosorbent assays (Tobe et al, Nucleic Acid Res, 1996; 24; 3728-32). For electrophoresis-based systems, use of a morbidity modifier tags or variation in probe length coupled with fluorescence detection enables the multiplex genotyping of several single nucleotide substitutions in a single tube (Baron et al, 1997; Clinical Chem., 43; 1984-6). When used on arrays, ASOs can be spotted at specific locations or addresses on a chip, PCR amplified DNA can then be added and ligation to labeled oligonucleotides at specific addresses on the array measured (Zhong et al, Proc Natl Acad Sci 2003; 100; 11559-64).

In some embodiments, single-base extension can be utilized to identify variances or a polymorphic site. Single base-extension or mini-sequencing involves annealing an oligonucleotide primer to the single strand of a PCR product and the addition of a single dideoxynucleotide by thermal DNA polymerase. The oligonucleotide is designed to be one base short of the mutation site. The dideoxynucleotide incorporated is complementary to the base at the mutation site. Approaches can use different fluorescent tags or haptens for each of the four different dideoxynucleotides (Pastinen et al, Clin Chem 1996, 42; 1391-7). The dideoxynucleotide differ in molecular weight and this is the basis for single-base extension methods utilizing mass-spectrometry, and genotyping based on the mass of the extended oligonucleotide primer, can be used, for example matrix-assisted laser adsorption/ionization time-of flight mass spectrometry or MALDI-TOF (Li et al, Electrophoresis, 1999, 20; 1258-65), which is quantitative and can be used to calculate the relative allele abundance making the approach suitable for other applications such as gene dosage studies (for example for estimation of allele frequencies on pooled DNA samples).

Mini-sequencing or Micro-sequencing by MALDI-TOF can be performed by means known by persons skilled in the art. In a variation of the MALDI-TOF technique, some embodiments can use the Sequenom's Mass Array Technology (www.sequenom.com) (Sauser et al, Nucleic Acid Res, 2000, 28; E13 and Sauser et al, Nucleic Acid Res 2000, 28: E100) and also the GOOD Assay (Sauer S et al, Nucleic Acid Res, 2000; 28, E13 and Sauer et al, Nucleic Acid Res, 2000; 28:E100).

In some embodiments, variations of MALDI-TOF can be performed for analysis of variances in the genes associated with SNPs described herein. For example, MALDI and electrospray ionization (ESI) (Sauer S. Clin Chem Acta, 2006; 363; 93-105) can also be used in various aspects described herein.

In some embodiments, hybridization based genotyping (e.g., Allele-Specific Amplification (ASA)) can be utilized to identify variances or a polymorphic site. Allele-specific Amplification is also known as amplification refractory mutation system (ARMS) uses allele specific oligonucleotides (ASO) PCR primers and is an well established and known PCR based method for genotyping (Newton et al, J Med Genet, 1991; 28; 248-51). Typically, one of the two oligonucleotide primers used for the PCR binds to the mutation site, and amplification only takes place if the nucleotide of the mutation is present, with a mismatch being refractory to amplification. The resulting PCR products can be analyzed by any means known to persons skilled in the art. In a variation of the approach, termed mutagenically separated PCR (MS-PCR) the two ARMS primer of different lengths, one specific for the normal gene and one for the mutation are used, to yield PCR products of different lengths for the normal and mutant alleles (Rust et al, Nucl Acids Res, 1993; 21; 3623-9). Subsequent gel electrophoresis, for example will show at least one of the two allelic products, with normal, mutant or both (heterozygote) genes. A further variation of this forms the basis of the Masscode System™ (www.bioserve.com) which uses small molecular weight tags covalently attached through a photo-cleavable linker to the ARMS primers, with each ARMS primers labeled with a tag of differing weight (Kokoris et al, 2000, 5; 329-40). A catalogue of numerous tags allows simultaneous amplification/genotyping (multiplexing) of 24 different targets in a single PCR reaction. For any one mutation, genotyping is based on comparison of the relative abundance of the two relevant mass tags by mass spectrometry.

Normal or mutant alleles can be genotyped by measuring the binding of allele-specific oligonucleotides (ASO) hybridization probes. In such embodiments, two ASO probes, one complementary to the normal allele and the other to the mutant allele are hybridized to PCR-amplified DNA spanning the mutation site. In some embodiments, the amplified products can be immobilized on a solid surface and hybridization to radiolabelled oligonucleotides such as known as a 'dot-blot' assay. In alternative embodiments, the binding of the PCR products containing a quantifiable label (e.g., biotin or fluorescent labels) to a solid phase allele-specific oligonucleotide can be measured. Alternatively, for a reverse hybridization assay, or "reverse dot-blot" the binding of PCR products containing a quantifiable label (for example but not limited to biotin or fluorescent labels) to a solid phase allele-specific oligonucleotide can be measured. In some embodiments, the use of microarrays comprising hundreds of ASO immobilized onto a solid support surfaces to form an array of ASO can also be used for large scale genotyping of multiple single polymorphisms simultaneously, for example Affymetrix GENECHIP® Mapping 10K Array, which can easily be performed by persons skilled in the art.

In some embodiments, homogenous assays can be utilized to identify variances or a polymorphic site. Homogenous assays, also called "closed tube" arrays, genomic DNA and all the reagents required for the amplification and genotyping are added simultaneously. Genotyping can be achieved without any post-amplification processing. In some embodiments, one such homogenous assay is the 5'flurogenic nuclease assay, also known as the TAQMAN® Assay (Livak et al, Genet Anal, 1999; 14:143-9) and in alternative embodiments Melting curve analyses of FRET probes are used. Such methods are carried out using "real-time" thermocyclers, and utilize two dual-labeled ASO hybridization probes complementary to normal and mutant alleles, where the two probes have different reported labels but a common quencher dye. In such embodiments, the changes in fluorescence characteristics of the probes upon binding to PCR products of target genes during amplification enables "real-time" monitoring of PCR amplification and differences in affinity of the fluorogenic probes for the PCR products of normal and mutant genes enables differentiation of genotypes. The approach uses two dual-labeled ASO hybridization probes complementary to the mutant and normal alleles. The two probes have different fluorescent reported dyes but a common quencher dye. When intact, the probes do not fluoresces due to the proximity of the reporter and quencher dyes. During annealing phase of PCR, two probes compete for hybridization to their target sequences, downstream of the primer sites and are subsequently cleaved by 5' nuclease activity of Thermophilis aquaticus (Taq) polymerase as the primer is extended, resulting in the separation of the reporter dyes from the quencher. Genotyping is determined by measurement of the fluorescent intensity of the two reporter dyes after PCR amplification. Thus, when intact the probes do not fluoresce due to the proximity of the quencher dyes, whereas during the annealing phase of the PCR the probes compete for hybridization of the target sequences and the separation of one of the probes from the quencher which can be detected.

In some embodiments, melting-curve analysis of FRET hybridization is another approach that can be used to detect the presence or absence of SNPs described herein. Briefly, the reaction includes two oligonucleotide probes which when in close proximity forms a fluorescent complex, where one probe often termed the "mutant sensor" probe is designed to specifically hybridize across the mutation site and the other probe (often referred to as the "anchor probe") hybridizes to an adjacent site. Fluorescent light is emitted by the "donor" excites the "acceptor" fluorophore creasing a unique fluorogenic complex, which only forms when the probes bind to adjacent sites on the amplified DNA. The "sensor" probe is complementary to either the normal or the mutant allele. Once PCR is complete, heating of the sample through the melting temperatures of the probe yields a fluorescent temperature curve which differs for the mutant and normal allele.

A variation of the FRET hybridization method is the LCGREEN™ method, which obviates the requirement for fluorescent labeled probes altogether. LCGREEN™ is a sensitive highly fluorogenic double-stranded DNA (dsDNA) binding dye that is used to detect the dissociation of unlabeled probes (Liew et al, Clin Chem, 2004; 50; 1156-64 and Zhou et al, Clin Chem, 2005; 51; 1761 2). The method uses unlabeled allele-specific oligonucleotides probes that are perfectly complementary either to the mutant or normal allele, and the mismatch of the ASO/template double strand DNA complex results in a lower melting temperature and an earlier reduction in fluorescent signal form the dsDNA binding dye with increasing temperature.

The OLA can also be performed by the use of FRET probes (Chen et al, Genome Res, 1998; 8: 549-56). In such an embodiment, the PCR/ligation mix contains PCR primers, a thermostable DNA polymerase without 5' exonuclease activity (to prevent the cleavage of ligation probes during the ligation phase), a thermostable DNA ligase as well as the oligonucleotides for the ligation reaction. The ligation of the ASO each have a different acceptor fluorophore and the third ligation oligonucleotide which binds adjacently to the ASO has a donor fluorophore. The three ligation oligonucleotides are designed to have a lower melting temperature than the annealing temperature for the PCR primers in order to prevent their interference in PCR amplification. Following PCR, the temperature is lowered to allow ligation to proceed. Ligation results in FRET between donor and acceptor dyes, and alleles can be discerned by comparing the fluorescence emission of the two dyes.

Further, variations of the homogenous PCR- and hybridization based techniques to detect polymorphisms can also be used to detect the presence or absence of SNP biomarkers described herein. For example, the use of Molecular Beacons (Tyagi et al, Nat Biotech 1998; 16; 49-53) and SCORPION® Probes (Thelwell et al, Nucleic Acid Res 2000; 28; 3752-61). Molecular Beacons are comprised of oligonucleotides that have fluorescent reporter and dyes at their 5' and 3' ends, with the central portion of the oligonucleotide hybridizing across the target sequence, but the 5' and 3' flanking regions are complementary to each other. When not hybridized to their target sequence, the 5' and 3' flanking regions hybridize to form a stem-loop structure, and there is little fluorescence because of the proximity of the reported and the quencher dyes. However, upon hybridization to their target sequence, the dyes are separated and there is a large increase in the fluorescence. Mismatched probe-target hybrids dissociate at substantially lower temperatures than exactly matched complementary hybrids. There are a number of variations of the "molecular Beacon" approach. In some embodiments, such a variation includes use of SCORPION® Probes which are similar but incorporate a PCR primer sequence as part of the probe (Thelwell et al, Nucleic Acid Res 2000; 28; 3752 61). In another variation, 'duplex' format gives a better fluorescent signal (Solinas et al, Nucleic Acid Res, 2001, 29; E96).

In another embodiment, polymorphisms can be detected by genotyping using a homogenous or real-time analysis on whole blood samples, without the need for DNA extraction or real-time PCR. Such a method is compatible with FRET and TAQMAN® (Castley et al, Clin Chem, 2005; 51; 2025-30) enabling extremely rapid screening for the particular polymorphism of interest.

In some embodiments, fluorescent polarization (FP) can be utilized to identify variances or a polymorphic site. In FP, the degree to which the emitted light remains polarized in a particular plane is proportional to the speed at which the molecules rotate and tumble in solution. Under constant pressure, temperature and viscosity, FP is directly related to the molecular weight of a fluorescent species. Therefore, when a small fluorescent molecule is incorporated into a larger molecule, there is an increase in FP. FP can be used in for genotyping of polymorphisms of interest (Chen et al, Genome Res, 1999; 9: 492-8 and Latif et al, Genome Res, 2001; 11; 436-40). FP can be utilized in 5' nuclease assay (as described above), where the oligonucleotide probe is digested to a lower molecule weight species, for example is amenable to analysis by FP, but with the added benefit of not requiring a quencher. For example, Perkin-Elmers AcycloPrime™-FP SNP Detection Kit can be used as a FP mini-sequencing method. Following PCR amplification, unincorporated primers and nucleotides are degraded enzymatically, the enzymes heat inactivated and a mini-sequencing reaction using DNA polymerase and fluorescent-labeled dideoxynucleotides performed. FP is then measured, typically in a 96- to 386-well plate format on a FP-plate reader.

In some embodiments, pyrosequencing can be used. The primer extension reaction and analysis is performed using PYROSEQUENCING™ (Uppsala, Sweden) which essentially is sequencing by synthesis. A sequencing primer, designed directly next to the nucleic acid differing between the disease-causing mutation and the normal allele or the different SNP alleles is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the mutation or polymorphism, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows a clear determination of the presence or absence of, for example, the mutation or polymorphism. Thereafter, apyrase, a nucleotide degrading enzyme, continuously degrades unincorporated dNTPs and excess ATP. When degradation is complete, another dNTP is added which corresponds to the dNTP present in for example the selected SNP. Addition of dNTPs is performed one at a time. Deoxyadenosine alfa-thio triphosphate (dATPS) is used as a substitute for the natural deoxyadenosine triphosphate (dATP) since it is efficiently used by the DNA polymerase, but not recognized by the luciferase. For detailed information about reaction conditions for the PYROSEQUENCING, see, e.g. U.S. Pat. No. 6,210,891, which is incorporated herein by reference.

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process which structure differs between the different alleles selected for detection, i.e. the disease-causing allele and the normal allele as well as between the different selected SNPs. Unlike the PCR-based methods, the INVADER® OS relies on linear amplification of the signal generated by the INVADER® process, rather than on exponential amplification of the target.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

Mutations or polymorphisms can also be detected using allele-specific hybridization followed by a MALDI-TOF-MS detection of the different hybridization products. In one embodiment, the detection of the enhanced or amplified nucleic acids representing the different alleles is performed using matrix-assisted laser desorption ionization/time-of-flight (MALDI-TOF) mass spectrometric (MS) analysis. This method differentiates the alleles based on their different mass and can be applied to analyze the products from the various above-described primer-extension methods or the INVADER® process.

In some embodiments, alterations in electrophoretic mobility are used to identify the particular allelic variant. For example, single strand conformation polymorphism (SSCP) can be used to detect differences in electrophoretic mobility between mutant and wild type nucleic acids (Orita et al. (1989) Proc Natl. Acad. Sol USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to the sequence, the resulting alteration in electrophoretic mobility enables the detection of even a single base change. Alterations in the mobility of the resultant products are thus indicative of a base change. Suitable controls and knowledge of the "normal" migration patterns of the wild-type alleles can be used to identify polymorphic variants. The DNA fragments can be labeled or detected with labeled probes. The sensitivity of the assay can be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for, example by adding a GC clamp of approximately 40 bp of high-melting GC rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Other methods for genetic screening can be used to detect the presence or absence of the SNP biomarkers described herein, for example, to detect mutations in genomic DNA, cDNA and/or RNA samples. Methods commonly used, or newly developed or methods yet unknown are encompassed for use in detection of the presence or absence of any of the SNP biomarkers described herein. Examples of newly discovered methods include for example, but are not limited to; SNP mapping (Davis et al, Methods Mol Biology, 2006; 351; 75-92); Nanogen Nano Chip, (keen-Kim et al, 2006; Expert Rev Mol Diagnostic, 6; 287-294); Rolling circle amplification (RCA) combined with circularable oligonucleotide probes (c-probes) for the detection of nucleic acids (Zhang et al, 2006: 363; 61-70), luminex XMAP system for detecting multiple SNPs in a single reaction vessel (Dunbar S A, Clin Chim Acta, 2006; 363; 71-82; Dunbar et al, Methods Mol Med, 2005; 114:147-1471) and enzymatic mutation detection methods (Yeung et al, Biotechniques, 2005; 38; 749-758).

In one embodiment, one method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

In such embodiments, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e. g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with 51 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

U.S. Pat. No. 4,946,773 describes an RNaseA mismatch cleavage assay that involves annealing single-stranded DNA or RNA test samples to an RNA probe, and subsequent treatment of the nucleic acid duplexes with RNaseA. For the detection of mismatches, the single-stranded products of the RNaseA treatment, electrophoretically separated according to size, are compared to similarly treated control duplexes. Samples containing smaller fragments (cleavage products) not seen in the control duplex are scored as positive. The use of RNaseI for mismatch detection is also described in literature from Promega Biotech. Promega markets a kit containing RNaseI that is reported to cleave three out of four known mismatches.

In one embodiment, a long-range PCR (LR-PCR) is used to detect mutations or polymorphisms. LR-PCR products are genotyped for mutations or polymorphisms using any genotyping methods known to one skilled in the art, and haplotypes inferred using mathematical approaches (e.g., Clark's algorithm (Clark (1990) Mol. Biol. Evol. 7:111-122).

For example, methods including complementary DNA (cDNA) arrays (Shalon et al., Genome Research 6(7):639-45, 1996; Bernard et al., Nucleic Acids Research 24(8): 1435-42, 1996), solid-phase mini-sequencing technique (U.S. Pat. No. 6,013,431, Suomalainen et al. Mol. Biotechnol. June; 15(2):123-31, 2000), ion-pair high-performance liquid chromatography (Doris et al. J. Chromatogr. A can 8; 806(1):47-60, 1998), and 5' nuclease assay or real-time RT-PCR (Holland et al. Proc Natl Acad Sci USA 88: 7276-7280, 1991), or primer extension methods described in the U.S. Pat. No. 6,355,433, can be used.

Another method to detect mutations or polymorphisms is by using fluorescence tagged dNTP/ddNTPs. In addition to the use of the fluorescent label in the solid phase mini-sequencing method, a standard nucleic acid sequencing gel can be used to detect the fluorescent label incorporated into the PCR amplification product. A sequencing primer is designed to anneal next to the base differentiating the disease-causing and normal allele or the selected SNP alleles. A primer extension reaction is performed using chain terminating dideoxyribonucleoside triphosphates (ddNTPs) labeled with a fluorescent dye, one label attached to the ddNTP to be added to the standard nucleic acid and another to the ddNTP to be added to the target nucleic acid.

Others have described using the MutS protein or other DNA-repair enzymes for detection of single-base mismatches. Alternative methods for detection of deletion, insertion or substitution mutations that can be used in the practice of various aspects described herein are disclosed in U.S. Pat. Nos. 5,849,483, 5,851,770, 5,866,337, 5,925,525 and 5,928,870, each of which is incorporated herein by reference.

In another embodiment, multiplex PCR procedures using allele-specific primers can be used to simultaneously amplify multiple regions of a target nucleic acid (PCT Application WO89/10414), enabling amplification only if a particular allele is present in a sample. Other embodiments using alternative primer-guided nucleotide incorporation procedures for assaying polymorphic sites in DNA can be used, and have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Nad. Acad. Sci. (USA) 88:1143-1147 (1991); Bajaj et al. (U.S. Pat. No. 5,846,710); Prezant, T. R. et al., Hum Mutat. 1: 159-164 (1992); Ugozzoli, L. et al., GATA 9:107-112 47 (1992); Nyr6n, P. et al., Anal. Biochem. 208:171-175 (1993)).

Other known nucleic acid amplification procedures include transcription-based amplification systems (Malek, L. T. et al., U.S. Pat. No. 5,130,238; Davey, C. et al., European Patent Application 329,822; Schuster et al.) U.S. Pat. No. 5,169,766; Miller, H. I. et al., PCT-Application WO89/06700; Kwoh, D. et al., Proc. Natl. Acad Sci. (USA) 86:1173 Z1989); Gingeras, T. R. et al., PCT Application WO88/10315)), or isothermal amplification methods (Walker, G. T. et al., Proc. Natl. 4cad Sci. (U.S.A) 89:392-396 (1992)) can also be used.

Another method to determine genetic variation is using "gene chips". The use of microarrays comprising a multiplicity of sequences is becoming increasingly common in the art. Accordingly, a microarray having at least one oligonucleotide probe, as described above, appended thereon, can be used for SNP genotyping.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes can also be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

Examples of identifying polymorphisms and applying that information in a way that yields useful information regarding patients can be found, for example, in U.S. Pat. No. 6,472,157; U.S. Patent Application Publications 20020016293, 20030099960, 20040203034; WO 0180896, all of which are hereby incorporated by reference.

In some embodiments, to determine the response of a human subject to a PAR4 inhibitor, the PAR4 polypeptide obtained from the subject can be sequenced to determine the identity of an amino acid at position 120 of SEQ ID NO: 1. If the amino acid is alanine, the subject can benefit from a PAR4 inhibitor. If the amino acid is threonine, the subject should avoid PAR4 inhibitors. Methods of sequencing polypeptides are known in the art. The two major direct methods of protein sequencing are mass spectrometry and the Edman degradation reaction.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

As used herein, the terms "treat," "treatment," "treating," or "amelioration" refer to therapeutic treatments, wherein the object is to reverse, alleviate, ameliorate, inhibit, slow down or stop the progression or severity of a condition involving PAR4, e.g., thrombosis. The term "treating" includes reducing or alleviating at least one adverse effect or symptom of a condition, e.g., thrombosis. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. For example, treatment is considered effective if thrombosis is prevented or the blood clot is dissolved. The term "treatment" of a disease also includes providing relief from the symptoms or side-effects of the disease (including palliative treatment). In one embodiment, at least one symptom of thrombosis is alleviated by at least about 10%, at least about 15%, at least about 20%, at least about 30%, at least about 40%, or at least about 50%. In another embodiment, at least one symptom is alleviated by more than 50%, e.g., at least about 60%, or at least about 70%. In one embodiment, at least one symptom is alleviated by at least about 80%, at least about 90% or greater, as compared to a control (e.g., a subject having the same or similar degree of thrombosis as the treated subject is administered without a PAR1 inhibitor).

As used herein, the term "administering," refers to the placement of a compound as disclosed herein into a subject by a method or route which results in at least partial delivery of the agent at a desired site. Pharmaceutical compositions can be administered by any appropriate route which results in an effective treatment in the subject, e.g. parenteral, intravenous, intralesional, or intratumoral.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G" a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length.

The term "oligonucleotide," as used herein refers to primers and probes described herein, and is defined as a nucleic acid molecule comprised of at least two or more ribo- or deoxyribonucleotides. The exact size of the oligonucleotide will depend on various factors and on the particular application and use of the oligonucleotide. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, an oligonucleotide probe typically contains 15-25 or more nucleotides, although it may contain fewer nucleotides. The probes as disclosed herein are selected to be substantially complementary to different strands of a particular target nucleic acid sequence. This means that the probes must be sufficiently complementary so as to be able to "specifically hybridize" or anneal with their respective target strands. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarily with the sequence of the target nucleic acid to anneal therewith specifically.

In the context of some embodiments of various aspects described herein, the term "probe" refers to a molecule which can detectably distinguish between target molecules differing in structure (e.g. nucleic acid or protein sequence). Detection can be accomplished in a variety of different ways depending on the type of probe used and the type of target molecule. Thus, for example, detection may be based on discrimination on detection of specific binding. Examples of such specific binding include antibody binding and nucleic acid, antibody binding to protein, nucleic acid binding to nucleic acid, or aptamer binding to protein or nucleic acid. Thus, for example, probes can include enzyme substrates, antibodies and antibody fragments, and preferably nucleic acid hybridization probes.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "complementary" or "complement" as used herein refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, such that at least about 50%, and preferably at least about 75%, at least about 90%, or at least about 95% or at least 100% of the nucleotide residues of the first portion are capable of base pairing with nucleotide residues in the second portion. More preferably, all nucleotide residues of the first portion are capable of base pairing with nucleotide residues in the second portion.

The terms "variant", "variance", "mutation" or "polymorphism" are used interchangeably herein, and refer to a difference in nucleic acid sequence among members if a population of individuals. Polymorphisms can sometimes be referred to as "single nucleotide polymorphism" or "SNP" when they vary at a single nucleotide. In some embodiments, polymorphisms can be synonymous or nonsynonymous. Synonymous polymorphisms when present in the coding region or non-coding region typically do not result in an amino acid change, but can result in altered mRNA stability or altered alternative splice sites. Nonsynonymous polymorphism, when present in the coding region, can result in the alteration of one or more codons resulting in an amino acid replacement in the amino acid chain. Such mutations and polymorphisms may be either heterozygous or homozygous within an individual. Homozygous individuals have identical alleles at one or more corresponding loci on homologous chromosomes, while heterozygous individuals have two different alleles at one or more corresponding loci on homologous chromosomes. A polymorphism is thus said to be "allelic," in that, due to the existence of the polymorphism, some members of a species carry a gene with one sequence (e.g., the normal or wild-type "allele"), whereas other members may have an altered sequence (e.g., the variant or, mutant "allele").

The term "genotype" refers to the specific allelic composition of an entire cell or a certain gene, whereas the term "phenotype" refers to the detectable outward manifestations of a specific genotype.

The term "allele", as used herein, refers to one member of a pair of different forms of a gene. As used herein alleles refer to coding and to non-coding sequences. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

Other than in the operating examples, or where otherwise indicated, all numbers expressing quantities of ingredients or reaction conditions used herein should be understood as modified in all instances by the term "about." The term "about" when used in connection with percentages may mean ±5% of the value being referred to. For example, about 100 means from 95 to 105.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology described herein is further illustrated by the following examples which in no way should be construed as being further limiting.

Example: Common Variants in the Human Platelet PAR4 Thrombin Receptor Alter Platelet Function and Differ by Race Methods The Platelet RNA and eXpression 1 (PRAX1) Study and Genotyping As described before,[20,21] 154 healthy individuals (70 black, 84 white) were recruited between 2010 and 2011. Subject race/ethnicity was initially classified by self-identification, but subsequently validated by Principal Component Analysis of 4.3 million genotypes from all 154 PRAX1 subjects.[20] Additional healthy, male and female subjects, self-identified as black or white race were recruited in Philadelphia (cohort 2) for platelet calcium and PAR inhibitor studies. These subjects were genotyped for rs773902 or rs2227346 using TAQMAN SNP Genotyping Assays (Life Technologies, Carlsbad, Calif., USA). Written informed consent was obtained from all participants and with the approval of the Institutional Review Boards of the Baylor College of Medicine and Thomas Jefferson University.

PAR4 Expression mRNA levels from leukocyte depleted platelets[22] were profiled using the Affymetrix Human Gene 1.0ST array (Affymetrix, Santa Clara, Calif., USA). Platelet protein lysates were separated by SDS-PAGE, transferred to nitrocellulose and probed with α-PAR4[23] or α-GAPDH antibodies (sc-25778, Santa Cruz Biotechnology, Dallas, Tex., USA). PAR4 and GAPDH bands were quantified using Image Studio software (Li-Cor, Lincoln, Neb., USA). Results are presented as PAR4 intensity normalized to GAPDH intensity.

Platelet Phenotyping

Platelet rich plasma was obtained from each participant and light transmission aggregometry was performed as described.[20,21] An integrated agonist response score (ARS) was developed that allowed precise differentiation among subjects with the same maximal aggregation. The score is the weighted average, determined by principal component analysis, of the max and slope of the aggregation curve measured by light transmission aggregometry in response to one or more concentrations of agonist. The concentrations used were: 0.5 mg/ml arachidonic acid; 4 μM ADP; 500, 750, or 2000 ng/ml α-CD9 antibody (Abcam, Cambridge, UK); 10 or 20 ng/ml collagen related peptide (CRP, synthesized at Baylor College of Medicine and crosslinked with glutaraldehyde); 1 or 2 μM PAR1-AP (GL Biochem, Shanghai, China); and 50 or 75 μM PAR4-AP (GL Biochem, Shanghai, China). This score correlated strongly with standard assessment of maximal percent aggregation, but inclusion of slope (a minor contributor to the overall score and highly related to maximal aggregation) allowed distinction among platelets from subjects with the same maximal aggregation value.[20]

Genotype Quantitative Trait Locus and Racial Variation Analyses

DNA from the buffy coats was hybridized to the HumanOmni5 array (Illumnia Inc., San Diego, Calif., USA). To evaluate associations between genotype markers and PAR4 ARS, a multiple regression framework was used that permits statistical adjustment to account for covariates potentially influencing the trait in addition to the genotype information that was the primary focus. The association between genotype markers within 50 kb of the F2RL3 transcription start and stop site and the PAR4 ARS was tested. To model an additive effect, genotype of each marker was converted into integer values [0, 1, 2], representing the number of copies of the major allele. This value was introduced to the multiple regression model as an independent variable (predictor) after controlling for other covariates including self-identified race, gender and age. The dependent variable is the PAR4 ARS, resulting in the following linear model equation:

$$Y=\beta_0+\beta_1 Age+\beta_2 Gender+\beta_3 Race+\beta_4 SNP+\epsilon$$

Here, Y represents the PAR4 ARS and $\epsilon$ is the stochastic error term. The $\beta_4$ coefficient and its corresponding standard error were estimated, and this model separately was evaluated for each genotype marker. The P-value for the $\beta_4$ coefficient from this linear regression was used to assign significance between each genotype marker and PAR4 ARS.

Human Genome Diversity Project (HGDP) data and geographical representation was obtained using the HGDP selection browser (http://hgdp.uchicago.edu/cgi-bin/gbrowse/HGDP/) from the Pritchard laboratory (University of Chicago). The underlying data was generated by Li et al.[24]

Calcium Mobilization

Washed platelets were resuspended to a final concentration of $1.0\times10^6$ platelets/mL in Tyrode's buffer (137 mM NaCl, 0.3 mM $Na_2HPO_4$, 2 mM KCl, 12 mM $NaHCO_3$, 5 mM HEPES pH 7.3, 5 mM glucose, 0.35% BSA) supplemented with 1 mM $CaCl_2$. Platelets were incubated with the cell permeable $Ca^{2+}$ sensitive dye, Fluo-4 AM, for ten minutes, stimulated with 50 μM PAR4-AP and mean fluorescence intensity (MFI) was measured in real-time on a flow cytometer for ten minutes to monitor the rise in free intracellular $Ca^{2+}$. Data is reported as the fold change comparing maximum MFI to the baseline MFI measured prior to platelet stimulation.

$IP_3$ Quantification

The expression vectors pBJ-FLAG-PAR4120A-296F, pBJ-FLAG-PAR4120A-296V, and pBJ-FLAG-PAR4120T-296V were generated by site directed mutagenesis from pBJ-FLAG-PAR4120T-296F[25] and sequenced for verification. $2.5 \times 10^6$ 293 HEK cells were transfected with 5 μg of vector using Lipofectamine 2000 (Life Technologies). 48 hours post-transfection, 10% of the cells were incubated 20 min at 37° C. with a FITC-α-FLAG antibody (F1804, Sigma-Aldrich, St. Louis, Mo.). Surface expression was quantified using an Accuri C6 flow cytometer (BD Biosciences, San Jose, Calif., USA). MFI was calculated using FlowJo software. The remaining 90% of cells were counted and then treated with 1 mM PAR4-AP or control. Samples were then lysed at 5, 30, or 600 seconds and $IP_3$ quantified using the Inositol-1,4,5-Trisphosphate [$^3H$] Radioreceptor Assay Kit (Perkin Elmer, Waltham, Mass., USA) following the manufacturer's protocol. Results were normalized to cell number and surface PAR4 expression.

Inhibitor Studies

Platelets were pre-incubated with the indicated concentrations of vorapaxar[26] (Axon Medchem, Reston, Va., USA) or YD-3 [1-benzyl-3-(ethoxycarbonylphenyl)-indazole][7] (a gift from Dr. Craig Lindsley at Vanderbilt University) as previously described.[27] Aggregation was then quantified after stimulation with 5 μM PAR1-AP or 100 μM PAR4-AP.

Statistical Analysis

Multiple linear regression analysis was performed including the PAR4 protein level and the risk SNPs as explanatory variables and PAR4 reactivity as the dependent variable. To determine fraction of variance of PAR4 reactivity explained by PAR4 protein levels and F2RL3 genotype, PAR4 protein level was brought into the model first followed by rs773902 genotype. To test for an interaction between rs773902 and YD-3, a linear regression was performed, using aggregation as the dependent variable and PAR4-AP concentration, YD3 concentration, and rs773902 genotype as dependent variables. All statistical analyses were implemented using the R statistical package,[28] SPSS v.19 (IBM, Armonk, N.Y., USA), or GraphPad Prism (GraphPad Software, La Jolla, Calif., USA). The linkage disequilibrium (LD) heatmap was generated using the R packages LDheatmap and genetics. There was no substantive racial difference in the linkage analysis of the F2RL3 region.

Results

Racial Difference in Platelet PAR4 Expression

Figure 1B:
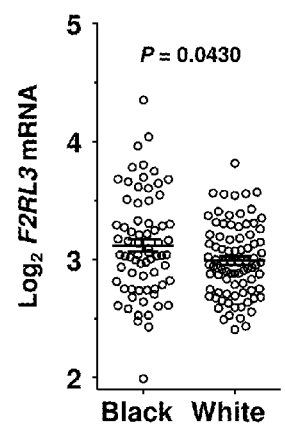
Figure 1C:
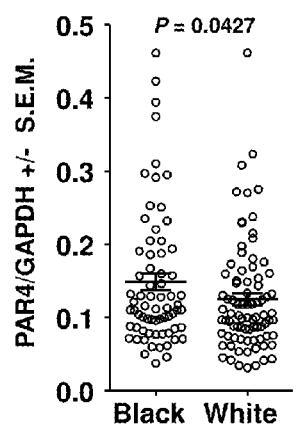
Figure 1D:
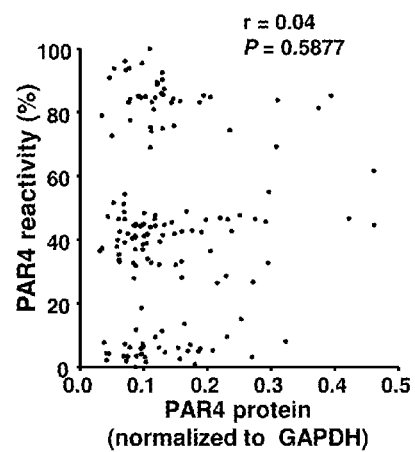

FIG. 1A shows greater PAR4 reactivity in platelets from 70 black subjects compared to 84 white ($p=6.8 \times 10^{-9}$) in the PRAX1 study. Regardless of race, there appeared to be 3 groups of PAR4-AP responders: high (>70%), intermediate (~30% to ~60%) and low (<20%). Such a finding would be consistent with an additive genetic effect, but whether quantitative differences in PAR4 protein expression might contribute to racial differences in platelet PAR4 reactivity was first considered. Using platelets from all 154 subjects it was found that blacks had 9% higher mean F2RL3 mRNA levels (P=0.043, FIG. 1B) and 14% PAR4 protein levels (P=0.0427, FIG. 1C). Although these small racial differences in PAR4 expression did not seem adequate to explain the 3.7-fold faster platelet aggregation in blacks[20] or the apparent 3 response groups, whether expression levels correlated with PAR4 reactivity was considered but none was observed (FIG. 1D). In addition, multiple linear regression analysis showed PAR4 protein level explained only 0.2% of the observed variation in PAR4 reactivity and that PAR4 protein was not explanatory for PAR4 reactivity (P=0.415).

F2RL3 Loci Associated with PAR4 Reactivity

We next considered whether a qualitative (or functional) difference in PAR4 might contribute to the racial difference in PAR4 reactivity. Quantitative trait locus (QTL) analysis of the PRAX1 cohort identified three F2RL3 SNPs, rs773904, rs773903 and rs773902, associated with platelet PAR4 reactivity (P-values of $1.26 \times 10^{-14}$, $1.26 \times 9.15 \times 10^{-16}$, respectively) after accounting for race, age and sex (FIG. 2A). Linear regression analysis indicated no association of PAR4 protein level with rs773904 (P=0.491), rs773903 (P=0.491) or rs773902 (P=0.489). rs773904 and rs773903 are intronic (FIG. 2B), whereas rs773902 is located in the second exon and alters residue 120 in the second transmembrane domain. The "G" allele of rs773902 encodes alanine (Ala) and the "A" allele encodes threonine (Thr). Since rs773902 is non-synonymous and in strong LD with the two intronic SNPs (FIG. 2B), the subsequent analyses was focused on rs773902. After controlling for protein level, the SNP rs773902 explains 48% of variability in PAR4 reactivity (by ANOVA partial sum of squares).

The allelic frequency of rs773902 in PRAX1 differed between self-identified blacks and whites ($P=4.31 \times 10^{-16}$, Fisher's Exact). The frequency of the G allele was 37% in blacks and 81% in whites (FIG. 2C). Conversely, the frequency of the A allele was 63% in black subjects but only 19% in whites. The HGDP[24] was queried to assess whether U.S. racial genotypes were similar to other geographic locations and found corresponding racial rs773902 allele frequencies: the A allele (most common in U.S. blacks) was most prevalent in sub-Saharan Africa and Papua New Guinea; the G allele (most common in U.S. whites) was more prevalent elsewhere (FIG. 2D).

Figure 3C:
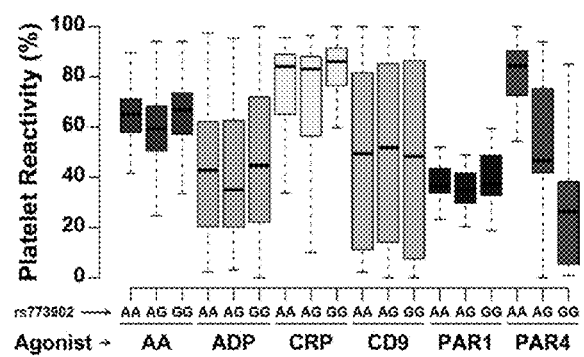

PAR4 Thr/Ala Dimorphism at Residue 120 and Phe/Val at Residue 296 Significantly Associate with Platelet PAR4 Function PAR4-mediated platelet aggregation significantly differed by rs773902 genotype in the whole cohort ($P=9.15 \times 10^{-16}$) (FIG. 3A) and within black and white subjects ($P=4.3 \times 10^{-9}$ and $P=3.1 \times 10^{-8}$ respectively) (FIG. 3B). Platelets from subjects homozygous for Thr120 (more common among blacks) achieved the highest average maximum aggregation in response to PAR4-AP, while platelets from subjects homozygous for Ala120 (more common among whites) achieved the lowest average maximum aggregation among both races. Heterozygotes showed an intermediate phenotype. F2RL3 rs773902 genotype showed no effect on the platelet aggregation response to arachidonic acid (P=0.0614), ADP (P=0.5656), collagen-related peptide (P=0.1639), α-CD9 antibody (P=0.6923) or PAR1-AP (P=0.2807) (FIG. 3C). Further analyses of arachidonic acid-induced platelet aggregation data showed no difference between Ala/Ala homozygotes and Thr/Thr homozygotes (P=0.6325, pair-wise T-test).

Figure 3D:
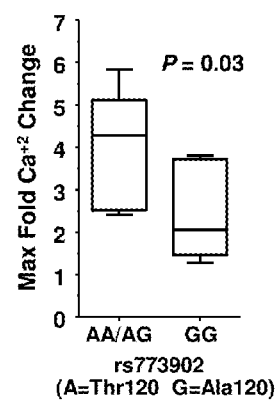

PAR4-mediated platelet activation results in $Ca^{2+}$ release. FIG. 3D shows that platelets from donors with either one or two copies of the PAR4-Thr120 variant underwent approximately 2-fold higher level of $Ca^{+2}$ flux compared to PAR4-Ala120 homozygotes in response to PAR4-AP stimulation (P=0.03).

Figure 3E:
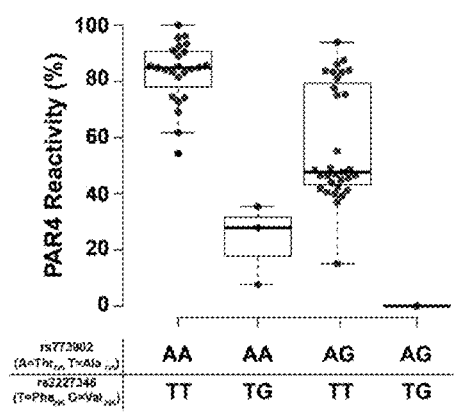

Additional analysis of the PRAX1 data identified a second non-synonymous F2RL3 SNP, rs2227346 not linked to rs773904, rs773903 or rs773902 (FIG. 2B). rs2227346 alters residue 296 in the $6^{th}$ transmembrane domain of PAR4; the common "T" allele encodes phenylalanine (Phe), and the less common "G" allele encodes valine (Val). No alleles from whites harbored the rs2227346 G variant. Although the numbers of Val-positive subjects were small in PRAX1, the presence of Val296 was associated with dramatically lower PAR4-mediated platelet aggregation compared to PAR4-296Phe (P=1.75×10$^{-8}$) (FIG. 3E).

The PAR4 Thr/Ala-120 and Phe/Val-296 Dimorphisms Alter PAR4 Signaling

Figure 4A:
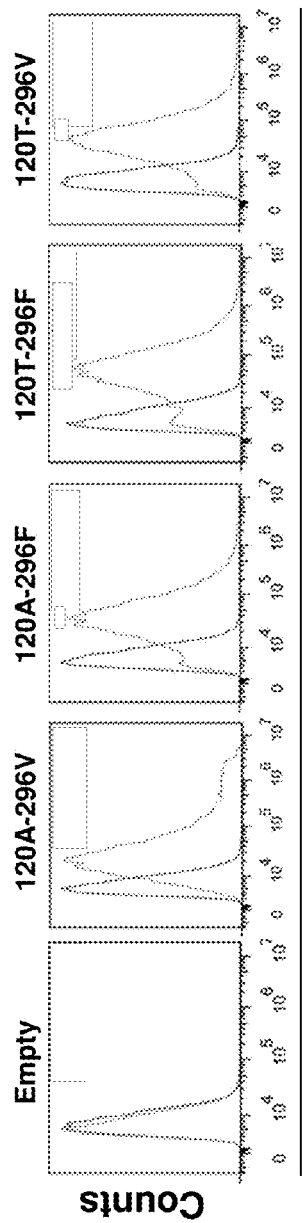
FIGS. 4A-4B show functional differences in $IP_3$ generation.
Figure 4B:
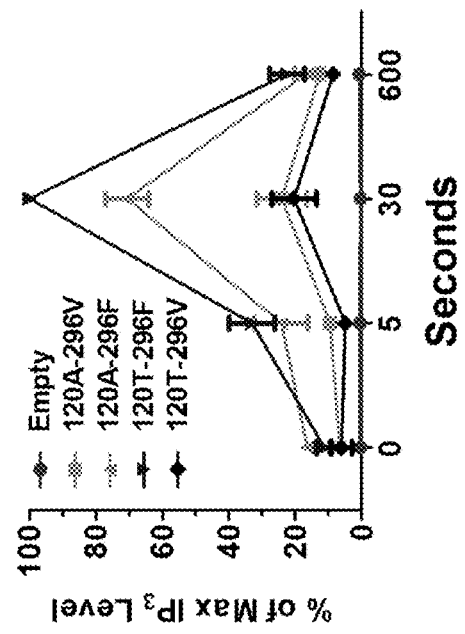
Figure 6A:
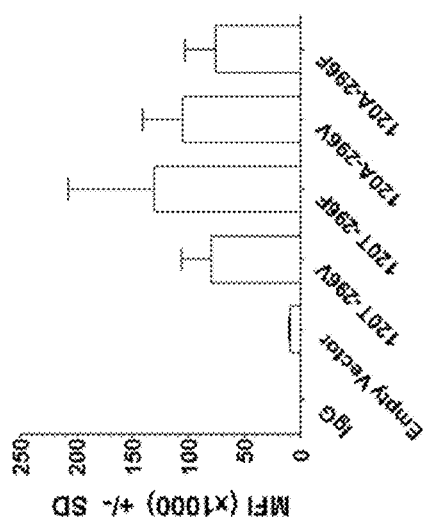
FIGS. 6A-6B show the effect of PAR4 variants on $IP_3$ generation in 293 HEK cells.
Figure 6B:
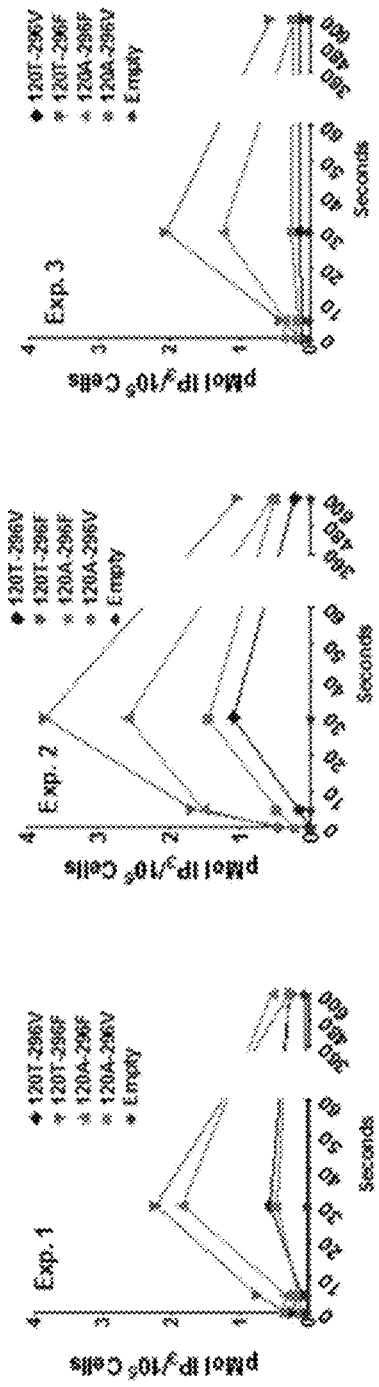

A proximal step in PAR4-induced platelet signal transduction upstream of calcium release is hydrolysis of phosphatidyl inositol 4,5-biphosphate (PIP2) to IP$_3$ and diacylglycerol (DAG).[29] To determine if these PAR4 variants differ in their capacity to generate IP$_3$, FLAG-tagged expression constructs for each of the four possible PAR4 alleles were generated. Transient transfection of each construct into 293 HEK cells demonstrated similar surface expression (one-way ANOVA, P=0.6543) (FIG. 4A, FIG. 6A). 48 hours after transfection, cells were stimulated with PAR4-AP and IP$_3$ was quantified. FIG. 4B shows that PAR4-Thr120-Phe296 generated more IP$_3$ than PAR4-Ala120-Phe296 (P=0.01, two-tailed T test at 30 s) and that Val296-containing variants showed less activity than either Phe296-containing variant. Absolute IP$_3$ quantification in pmol generated from each of the three independent experiments is shown in FIG. 6B. There was no correlation between variant surface expression and IP$_3$ generation (Pearson r=0.3783, P=0.2253).

The PAR4-Thr120 Variant is Resistant to Pharmacological Inhibition by YD-3

Figure 5A:
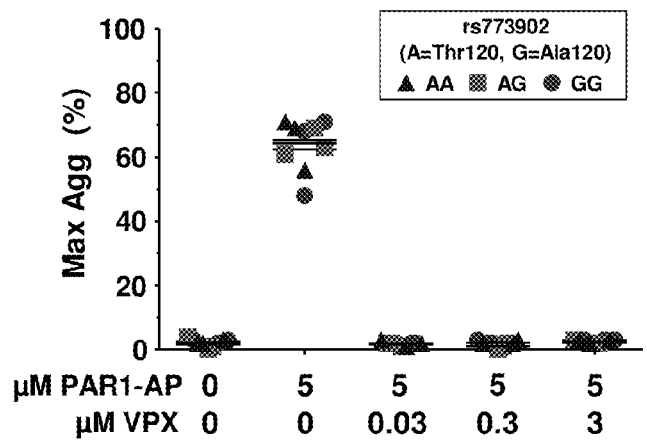
FIGS. 5A-5C show PAR4 variants are differentially susceptible to pharmacological inhibition. Platelets from donors genotyped for rs773902 were washed, incubated with the indicated concentrations of vorapaxar (VPX) (FIGS. 5A, 5B) or YD-3 (FIG. 5C) and then stimulated with (FIG. 5A) 5 μM PAR1-AP or (FIGS. 5B, 5C) 100 μM PAR4-AP. Aggregation was measured using light transmission aggregometry. n=3 each genotype. Horizontal lines indicate mean. (P=0.02).
Figure 5B:
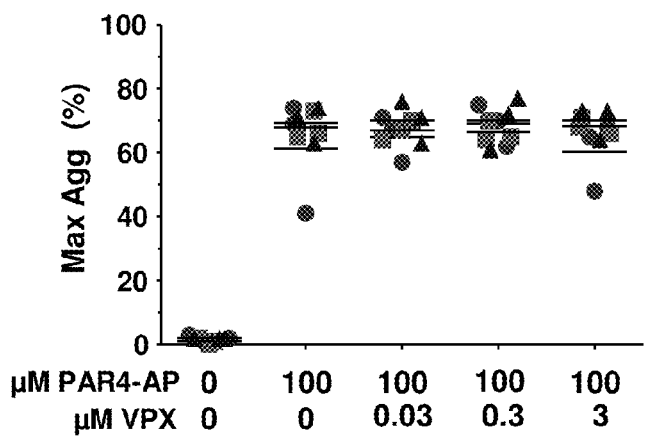
Figure 5C:
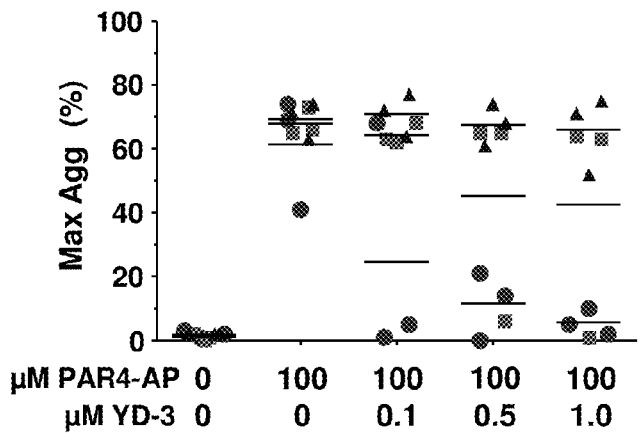

Recently there has been an increasing interest in the therapeutic potential of PAR inhibitors as anti-thrombotic agents. It was sought to determine whether the common Ala120Thr PAR4 variant might affect pharmacological inhibition of either PAR1 or PAR4. As expected, vorapaxar efficiently inhibited platelet aggregation through PAR1 (FIG. 5A) but had no effect on PAR4-induced platelet aggregation regardless of rs773902 genotype (FIG. 5B). YD-3 is a synthetic, low molecular weight, non-peptide indazole derivative that specifically blocks PAR4-induced platelet aggregation.[7,30] A significant interaction between genotype and YD-3 inhibitor on the PAR4-induced aggregation response was found (P=0.02) (FIG. 5C). Individuals homozygous for PAR4-Thr120 were resistant to up to 1 µM YD-3 inhibition, whereas platelets from PAR4-Ala120 homozygotes were inhibited by 0.5 µM YD-3; heterozygotes appeared to have an intermediate response.

Discussion

There is a racial disparity in CHD outcomes and platelets from healthy black subjects are hyperreactive through the PAR4 thrombin receptor compared to platelets from whites. The genetic and molecular mechanisms that contribute to racial differences in human platelet function was investigated herein. The major findings were the identification of: (1) racial differences in the frequency of common alleles of the PAR4-encoding gene, F2RL3, with whites having a high frequency of the Ala120 variant and blacks having a high frequency of the Thr120 variant; (2) an effect of the Ala120Thr on platelet PAR4 function wherein the Thr120 allele was associated with greater platelet aggregation, accounted for 48% of the variance in human platelet PAR4 reactivity and induced greater signaling; and, (3) an effect of the Ala120Thr variant on the inhibitory capacity of the PAR4 inhibitor, YD-3. These findings have important implications for risk, outcome and management of CHD.

There is a pronounced variation of 0 to 100% in the platelet aggregation response to PAR4-AP in the PRAX1 cohort, with platelets from black subjects showing greater reactivity than platelets from whites. PC-TP was previously shown to account for a portion of this racial difference, but ~82% of the variance remained unexplained. It was found that platelets from blacks expressed an average of 14% more PAR4 protein than platelets from whites. Although a small change in a surface receptor expression could theoretically have a larger effect on platelet aggregation, several aspects of the data do not support this possibility. First, there was no correlation between protein levels and PAR4-mediated platelet reactivity. Second, regression analysis indicated the protein levels accounted for only 0.2% of the observed variation in PAR4 reactivity. Third, the distribution of protein levels (FIG. 1C) did not resemble the distribution of PAR4 reactivity (FIG. 1A). For these reasons and because the three groups of PAR4 reactivity (high, intermediate and low) were consistent with the possibility of three genotypes, a genetic basis for the racial difference in PAR4 reactivity was considered.

Three SNPs within F2RL3 met genome-wide significance for associations with PAR4-mediated platelet reactivity. These SNPs map within 501 base pairs of one another and are in very strong linkage disequilibrium. Two of these three are intronic. In addition to rs773902, public databases were searched and reports of 10 other missense SNPs in F2RL3 were found. However, each of these has a minor allele frequency of less than 1%, making it implausible that these could account for the association between rs773902 and platelet aggregation in the 154 subject PRAX1 study. Blacks in PRAX1 more commonly express the rs773902 Thr120 allele, whereas whites more commonly express the Ala120 allele. The similar allele frequencies by race between PRAX1 and the HGDP argue against a U.S.-specific finding, and suggest the data may apply more broadly to global populations.

Only two large genome-wide studies have been performed testing for associations with platelet function. The first (from Framingham and Johns Hopkins) did not use agonists that activate platelets through PAR1 or PAR4.[31] The second study was PRAX1.[32] Prior GWAS "hits" in F2RL3 associated with clinical thrombotic disease have not been identified, but most studies were under-represented with black patients. The Thr120 allele in the white population is only 16% and perhaps these studies were not powered to identify associations among relatively infrequent variants such as this. Muehlschlegel et al performed a candidate locus substudy of the CABG Genomics Program and reported an association between rs773857 and PAR4-AP mediated platelet P-selectin expression. This SNP is in the CPAMD8 gene, ~18 kb downstream of F2RL3, but has no linkage to the F2RL3 SNPs described herein.[33]

The rs773902 genotype was strongly associated with PAR4-induced platelet aggregation and calcium release but not with the platelet aggregation response to other agonists, further supporting a PAR4-specific effect. A second amino acid-changing variant was identified, but only in black subjects. Transfection studies showed PAR4-Val296 traffics to the membrane but does not signal normally. Intriguingly, the valine for phenylalanine substitution functioned as a hypomorphic allele whose effect was dominant over the Thr120/Thr120 or Ala120/Thr120 variants. Because of the low frequency of this allele, it is difficult to make firm conclusions about its effect in human platelets.

To assess the biochemical effects of amino acid changes on downstream signaling events, 293 cells were used, which contain the appropriate components (the Gq pathway) and have been a standard in the platelet biology field.[34-36] Using PAR4-AP-induced IP$_3$ generation, an important PAR4 signaling molecule,[11,37] over-expression of the PAR4 variants demonstrated differing signaling capacities. Taken together, the simplest explanation for these genetic and cell biologic studies is that these functional variants alter platelet function.

The mechanism by which F2RL3 variants affect function is unclear, but the data raises a number of hypotheses. The greater $Ca^{2+}$ flux in platelets and enhanced $IP_3$ generation in 293 cells expressing PAR4-Thr120 suggests greater Gq-induced activation of PLCI3. Brian Kobilka and colleagues have shown in other seven-transmembrane G-protein coupled receptors, the transmembrane core of the protein undergoes conformational changes upon activation, affecting G-protein interaction.[38] In addition, a Thr (polar) substitution for Ala (nonpolar) at residue 120 may affect the interaction between the receptor and cholesterol and possibly affect both dimerization and ligand affinity.[39] Regarding the less common Phe296Val variant in transmembrane helix 6, this residue is predicted to lie in the ligand binding pocket of GPCR structures, and a valine substitution is predicted to alter ligand binding properties (http://www.gper.org/7tm/). Future crystal structure information for these variants may address these possibilities.

PAR4 inhibition may be an attractive alternative to PAR1 blockade by reducing the prolonged effects of thrombin while retaining the transient signaling mediated by an intact PAR1 pathway. In addition to blocking PAR4- but not PAR1-induced platelet aggregation,[7,30] YD-3 also blocks thrombin-induced platelet recruitment and smooth muscle cell proliferation, as well as neutrophil-induced platelet aggregation.[7,40,41] Oral YD-3 also attenuates intimal thickening in a rat carotid balloon injury model.[41] There was no prior assessment of a pharmacogenetic interaction between YD-3 (or any PAR inhibitor) and rs773902 for PAR4-induced platelet aggregation. The data demonstrate a potent interaction between the PAR4 Ala120Thr variant and YD-3 inhibition of PAR4-induced platelet aggregation. Without wishing to be bound by theory, it was hypothesized that YD-3 induces conformational changes in PAR4, and the extent of the conformational change is regulated by the amino acid at residue 120. Crystal structure data of the two receptor isoforms with YD-3 may help elucidate the basic molecular mechanism of this pharmacogenetic effect.

In summary, the F2RL3 variants described in this work contribute to a major fraction of the racial variance in human platelet PAR4 reactivity. The common PAR4 Ala120Thr variants lead to different downstream signaling events and pharmacogenetic interactions, and the rs773902 genotype may be more important than self-identified race for predicting risk and benefit in CVD. Lastly, and perhaps most importantly, these data suggest that YD-3 could benefit whites more than blacks and PAR4 hyperreactivity in blacks may negate some of the vorapaxar benefit. These apparent racial disparities support a need to develop new PAR4-inhibitors that effectively block the PAR4-Thr120 variant, compounds that may be especially beneficial to patients with African ancestry.

REFERENCES

1. Berry J D, Dyer A, Cai X, et al. Lifetime risks of cardiovascular disease. N Engl J Med. 2012; 366(4):321-329.
2. Thomas K L, Honeycutt E, Shaw L K, Peterson E D. Racial differences in long-term survival among patients with coronary artery disease. Am Heart J. 2010; 160(4): 744-751.
3. Eagle K A, Ginsburg G S, Musunuru K, et al. Identifying patients at high risk of a cardiovascular event in the near future: current status and future directions: report of a national heart, lung, and blood institute working group. Circulation. 2010; 121(12):1447-1454.
4. Bray P F, Mathias R A, Faraday N, et al. Heritability of platelet function in families with premature coronary artery disease. J Thromb Haemost. 2007; 5(8):1617-1623.
5. Bray P F, Mathias R A, Herrera-Galeano J E, et al. Heritability of platelet reactivity in White and African American subjects at moderately high risk of coronary artery disease. Circulation. 2005; 112:443a.
6. O'Donnell C J, Larson M G, Feng D, et al. Genetic and environmental contributions to platelet aggregation: the Framingham heart study. Circulation. 2001; 103(25): 3051-3056.
7. Wu C C, Hwang T L, Liao C H, et al. Selective inhibition of protease-activated receptor 4-dependent platelet activation by YD-3. Thromb Haemost. 2002; 87(6):1026-1033.
8. Covic L, Misra M, Badar J, Singh C, Kuliopulos A. Pepducin-based intervention of thrombin-receptor signaling and systemic platelet activation. Nat Med. 2002; 8(10):1161-1165.
9. Hollenberg M D, Saifeddine M. Proteinase-activated receptor 4 (PAR4): activation and inhibition of rat platelet aggregation by PAR4-derived peptides. Can J Physiol Pharmacol. 2001; 79(5):439-442.
10. Coughlin S R. Protease-activated receptors in hemostasis, thrombosis and vascular biology. J Thromb Haemost. 2005; 3(8):1800-1814.
11. Shapiro M J, Weiss E J, Faruqi T R, Coughlin S R. Protease-activated receptors 1 and 4 are shut off with distinct kinetics after activation by thrombin. J BiolChem. 2000; 275(33):25216-25221.
12. Holinstat M, Voss B, Bilodeau M L, McLaughlin J N, Cleator J, Hamm H E. PAR4, but not PAR1, signals human platelet aggregation via Ca2+ mobilization and synergistic P2Y12 receptor activation. J Biol Chem. 2006; 281(36):26665-26674.
13. Lova P, Campus F, Lombardi R, et al. Contribution of protease-activated receptors 1 and 4 and glycoprotein Ib-IX-V in the G(i)-independent activation of platelet Rap1B by thrombin. J Biol Chem. 2004; 279(24):25299-25306.
14. De Candia E, Hall S W, Rutella S, Landolfi R, Andrews R K, De Cristofaro R. Binding of thrombin to glycoprotein Ib accelerates the hydrolysis of PAR1 on intact platelets. J Biol Chem. 2001; 276(7):4692-4698.
15. Macfarlane S R, Seatter M J, Kanke T, Hunter G D, Plevin R. Proteinase-activated receptors. Pharmacol Rev. 2001; 53(2):245-282.
16. Henriksen R A, Hanks V K. PAR4 agonist AYPGKF stimulates thromboxane production by human platelets. Arterioscler Thromb Vasc Biol. 2002; 22(5):861-866.
17. Derian C K, Damiano B P, Addo M F, et al. Blockade of the thrombin receptor protease-activated receptor-1 with a small-molecule antagonist prevents thrombus formation and vascular occlusion in nonhuman primates. J Pharmacol Exp Ther. 2003; 304(2):855-861.
18. Tello-Montoliu A, Tomasello S D, Ueno M, Angiolillo D J. Antiplatelet therapy: thrombin receptor antagonists. Br J Clin Pharmacol. 2011; 72(4):658-671.
19. Young S E, Duvernay M T, Schulte M L, Lindsley C W, Hamm H E. Synthesis of indole derived protease-activated receptor 4 antagonists and characterization in human platelets. PLoS One. 2013; 8(6):e65528.

20. Edelstein L C, Simon L M, Montoya R T, et al. Racial differences in human platelet PAR4 reactivity reflect expression of PCTP and miR-376c. Nat Med. 2013; 19(12):1609-1616.
21. Simon L M, Edelstein L C, Nagalla S, et al. Human platelet microRNA-mRNA networks associated with age and gender revealed by integrated plateletomics. Blood. 2014; 123(16):e37-45.
22. Nagalla S, Shaw C, Kong X, et al. Platelet microRNA-mRNA coexpression profiles correlate with platelet reactivity. Blood. 2011; 117(19):5189-5197.
23. Mumaw M M, de la Fuente M, Arachiche A, Wahl III J K, Nieman M T. Preparation of monoclonal antibodies targeted to protease activated receptor 4 (PAR4). In Preparation. 2014.
24. Li J Z, Absher D M, Tang H, et al. Worldwide human relationships inferred from genome-wide patterns of variation. Science. 2008; 319(5866):1100-1104.
25. Shapiro M J, Trejo J, Zeng D, Coughlin S R. Role of the thrombin receptor's cytoplasmic tail in intracellular trafficking. Distinct determinants for agonist-triggered versus tonic internalization and intracellular localization. J Biol Chem. 1996; 271(51):32874-32880.
26. Chackalamannil S, Wang Y, Greenlee W J, et al. Discovery of a novel, orally active himbacine-based thrombin receptor antagonist (SCH 530348) with potent antiplatelet activity. J Med Chem. 2008; 51(11):3061-3064.
27. Zhang C, Srinivasan Y, Arlow D H, et al. High-resolution crystal structure of human protease-activated receptor 1. Nature. 2012; 492(7429):387-392.
28. R Core Team. R: A Language and Environment for Statistical Computing. Vienna, Austria: R Foundation for Statistical Computing; 2013.
29. Li Z, Delaney M K, O'Brien K A, Du X. Signaling during platelet adhesion and activation. Arterioscler Thromb Vasc Biol. 2010; 30(12):2341-2349.
30. Wu C C, Teng C M. Comparison of the effects of PAR1 antagonists, PAR4 antagonists, and their combinations on thrombin-induced human platelet activation. Eur J Pharmacol. 2006; 546(1-3):142-147.
31. Johnson A D, Yanek L R, Chen M H, et al. Genome-wide meta-analyses identifies seven loci associated with platelet aggregation in response to agonists. Nat Genet. 2010; 42(7):608-613.
32. Edelstein L C, Simon L M, Montoya R T, et al. Racial differences in human platelet PAR4 reactivity reflect expression of PCTP and miR-376c. Nat Med. 2013.
33. Muehlschlegel J D, Perry T E, Liu K Y, et al. Polymorphism in the protease-activated receptor-4 gene region associates with platelet activation and perioperative myocardial injury. Am J Hematol. 2011.
34. Zhu J, Choi W S, McCoy J G, et al. Structure-guided design of a high-affinity platelet integrin alphaIIbbeta3 receptor antagonist that disrupts Mg(2)(+) binding to the MIDAS. Sci Transl Med. 2012; 4(125):125ra132.
35. Kim S, Jin J, Kunapuli S P. Akt activation in platelets depends on Gi signaling pathways. J Biol Chem. 2004; 279(6):4186-4195.
36. Zhu L, Bergmeier W, Wu J, et al. Regulated surface expression and shedding support a dual role for semaphorin 4D in platelet responses to vascular injury. Proc Natl Acad Sci USA. 2007; 104(5):1621-1626.
37. Xu W F, Andersen H, Whitmore T E, et al. Cloning and characterization of human protease-activated receptor 4. Proc Natl Acad Sci USA. 1998; 95(12):6642-6646.
38. Rasmussen S G, DeVree B T, Zou Y, et al. Crystal structure of the beta2 adrenergic receptor-Gs protein complex. Nature. 2011; 477(7366):549-555.
39. Isberg V, Vroling B, van der Kant R, Li K, Vriend G, Gloriam D. GPCRDB: an information system for G protein-coupled receptors. Nucleic Acids Res. 2014; 42(Database issue):D422-425.
40. Wu C C, Hwang T L, Liao C H, Kuo S C, Lee F Y, Teng C M. The role of PAR4 in thrombin-induced thromboxane production in human platelets. Thrombosis and Haemostasis. 2003; 90(2):299-308.
41. Peng C Y, Pan S L, Guh J H, et al. The indazole derivative YD-3 inhibits thrombin-induced vascular smooth muscle cell proliferation and attenuates intimal thickening after balloon injury. Thromb Haemost. 2004; 92(6):1232-1239.

What is claimed is:

1. A method of preventing or treating thrombosis in a human subject in need thereof, the method comprising administering a therapeutically effective amount of a PAR4 inhibitor to a human subject determined to have a "G" allele for a single-nucleotide polymorphism (SNP) at rs773902.

2. The method of claim 1 wherein the method of preventing or treating thrombosis in a human subject further comprises, wherein (a) the human subject is being administered a PAR1 inhibitor and (b) has a "G" allele for a single-nucleotide polymorphism (SNP) at rs773902; the method comprising (a) stopping administration of the PAR1 inhibitor and (b) administering a therapeutically effective amount of a PAR4 inhibitor.

3. The method of claim 1, wherein the PAR4 inhibitor is selected from the group consisting of ethyl 4-(1-benzyl-1H-indazol-3-yl)benzoate (YD-3), trans-cinnamoyl-YPGKF-amide, P4pal-i1, and palmitoyl-SGRRYGHALR-amide (P4pal-10).

4. The method of claim 1, wherein the thrombosis is associated with coronary artery disease, stroke, vascular thrombosis, arterial thrombosis, atherothrombosis, deep vein thrombosis, peripheral vascular disease, peripheral arterial disease, or an inflammatory disease.

5. The method of claim 1, further comprising testing a sample from the human subject to determine the genotype of the SNP at rs773902.

6. The method of claim 5, wherein the sample is a blood sample, a urine sample, a buccal sample, a saliva sample, or a hair sample.

7. The method of claim 1, further comprising administering a therapeutically effective amount of a P2Y12 inhibitor to the subject selected from the group consist of: clopidogrel, prasugrel, ticagrelor, or cangrelor, a salt thereof, or a combination thereof.

\* \* \* \* \*